United States Patent [19]

Kuhla et al.

[11] Patent Number: 4,638,001

[45] Date of Patent: * Jan. 20, 1987

[54] BICYCLIC BENZENOID AMINOALKYLENE ETHERS AND THIOETHERS, PHARMACEUTICAL COMPOSITIONS AND USE

[75] Inventors: Donald E. Kuhla, Doylestown; Henry F. Campbell, Lansdale; William L. Studt, Harleysville, all of Pa.

[73] Assignee: William H. Rorer, Inc., Fort Washington, Pa.

[ * ] Notice: The portion of the term of this patent subsequent to Jul. 16, 2002 has been disclaimed.

[21] Appl. No.: 604,813

[22] Filed: Apr. 27, 1984

Related U.S. Application Data

[63] Continuation-in-part of Ser. No. 489,702, Apr. 29, 1983, Pat. No. 4,529,723.

[51] Int. Cl.$^4$ .................. A61K 31/41; A61K 31/535; C07D 249/12; C07D 413/12

[52] U.S. Cl. .................. 514/212; 546/276; 546/278; 514/222; 546/279; 548/200; 514/228; 548/265; 548/266; 514/230; 548/267; 260/244.4; 514/232; 260/245.5; 514/340; 514/234; 514/341; 544/58.7; 514/236; 514/237; 514/255; 514/314; 514/318; 514/319; 514/326; 514/343; 514/365; 514/383; 514/384; 514/340; 514/341; 544/58.5; 544/60; 544/62; 544/79; 544/128; 544/131; 544/132; 544/133; 544/58.7; 546/167; 546/187; 546/194; 546/205; 546/206

[58] Field of Search .................. 544/58.5, 60, 132, 62, 544/58.7, 79, 128, 131, 133; 546/205, 206, 167, 187, 194, 276, 278, 279; 548/267, 200, 265, 266; 260/245.5, 244.4; 514/212, 222, 232, 237, 255, 319, 383, 228, 230, 234, 236, 314, 318, 326, 340, 341, 343, 365, 384

[56] References Cited

U.S. PATENT DOCUMENTS 4,318,913 3/1982 Clitherow et al. .................. 548/267
4,529,723 7/1985 Kuhla et al. .................. 514/212

Primary Examiner—Robert W. Ramsuer
Attorney, Agent, or Firm—James A. Nicholson; Alexis Barron; Martin F. Savitzky

[57] ABSTRACT

A class of bicyclic benzenoid aminoalkylene ether and thioether compounds exhibiting pharmacological activity, including anti-secretory and anti-ulcerogenic activity, pharmaceutical compositions comprising these compounds, and methods for the treatment of gastrointestinal hyperacidity and ulcerogenic disorders in mammals using said compositions.

21 Claims, No Drawings

BICYCLIC BENZENOID AMINOALKYLENE ETHERS AND THIOETHERS, PHARMACEUTICAL COMPOSITIONS AND USE

This application is a continuation-in-part of U.S. Application Ser. No. 489,702, filed on Apr. 29, 1983, now U.S. Pat. No. 4,529,723.

FIELD OF THE INVENTION

This invention relates to a class of bicyclic benzenoid compounds characterized by an ether or thioether substituent on the phenyl ring and an exocyclic nitrogen substituent on the other ring of the bicyclic ring system and methods for the treatment of physiological disorders, including gastrointestinal disorders in humans and other mammals.

REPORTED DEVELOPMENTS

Gastrointestinal hyperacid secretion, stomach and intestinal ulceration, and gastritis are major gastrointestinal disorders observed in the general adult populations of industrialized societies. Many factors, including the production of excess gastric acid and the weakening of the lining of the stomach and gastrointestinal tract against such acid are implicated as causes of these disorders. Traditional treatment of these disorders has involved the administration of antacids to neutralize the excess gastric acid and the administration of antisecretory drugs which generally reduce the production of all gastric secretions.

In the last few years, the treatment of gastrointestinal disorders such as peptic ulcer has changed to include the use of anti-secretory drugs which selectively block the production of gastric acid. These drugs are believed to interfere with the body's physiological pathway responsible for the production of gastric acid by blocking the action of histamine. Histamine production is induced in the body by a number of stimuli, including stress, allergic reaction, etc., and acts to increase gastric secretion, dilate blood vessels and stimulate smooth muscle tissue. Histamine is believed to function by way of interaction with histamine receptors in the body. The subdivision of these receptors into two groups, the $H_1$- and $H_2$-receptors, was proposed by Ash and Schild (Brit. J. Pharmacol. Chemother, 1966, 27, 427) and Black et al (Nature 1972, 236, 385). The $H_1$-receptor is involved in the bronchial and gastrointestinal smooth muscle stimulative action of histamine. Drugs which block this action are labelled "antihistamines" (e.g. mepyramine).

Black et al, cited above, described the group of substances which act at histamine receptors other than the $H_1$-receptor as the $H_2$-receptors. Blocking the action of histamine at the $H_2$-receptors will selectively block histamine's stimulative action on gastric acid secretion and heart rate. Burimamide was the first clinically effective $H_2$-receptor antagonist inhibiting gastric secretion in man; but Burimamide's oral absorptivity is poor. Subsequent studies developed the orally active Metiamide, the side effects of which limited clinical use, and Cimetidine which has been marketed as an anti-ulcer drug. A number of classes of heterocyclic chemical compounds have been reported as $H_2$-receptor antagonists, for example, those disclosed in U.S. Pat. Nos. 4,104,381, 4,279,819, 4,323,566, 4,390,701, 4,395,553, and British published patent applications GB No. 2067987A and GB No. 2047238A, and EPO publication No. 0081955A2, the disclosures of which are incorporated by reference.

Another method for the prevention or treatment of gastric ulcer comprises the use of drugs which neither neutralize nor inhibit the secretion of gastric acid. These drugs constitute a class of anti-ulcer compounds which function to enhance the normal defense mechanisms of the body, rather than to reduce normal body secretions, and are described as "cytoprotective" agents. It has been proposed that such agents act to strengthen the mucosal lining of the gastrointestinal system by one or more mechanisms, thereby preventing any damage which could result from the action of strong gastric acid. Prostaglandins have been implicated in the mechanism of cytoprotection by a number of workers in the field. See, the discussion of cytoprotection in Robert, Andre, "Prostaglandins and Digestive Diseases", *Advances in Prostaglandin and Thromboxane Research*, Vol. 8 (Raven Press, N.Y. 1980), and Robert et al, "Cytoprotection by Prostaglandins in Rats", *Gastroenterology*, 77, 433–443 (1979), hereby incorporated by reference. Drugs, other than prostaglandins, which exhibit cytoprotective activity include carbenoxolone sodium, reported to exhibit undesirable side effects, such as edema, diastolic hypertension or hypokalemia, and the thiazol-2-yl-carbamoylcarboxylic acids, esters and imides described in U.S. Pat. No. 4,321,372.

Compounds of the present invention comprise bicyclic benzenoids which exhibit anti-secretory activity, $H_2$-receptor antagonist activity, anti-ulcer activity and cytoprotective activity.

SUMMARY OF THE INVENTION

This invention comprises a class of compounds according to Formula I

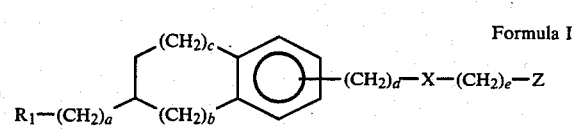

Formula I wherein:
a is 0, 1 or 2;
b is 0 or 1;
c is b, 1-b, 2-b or 3-b;
d is 0 or 1;
e is 2, 3 or 4;
X is oxygen, sulfur,

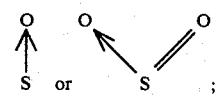

Z is —NHR$_4$,

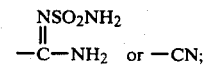
or —CN;

R$_1$ is —NR$_2$R$_3$,

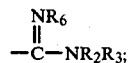

R$_2$ and R$_3$ are each independently H or alkyl, or both together with the nitrogen to which they are attached form a 5, 6 or 7-membered ring which may include one to three additional hetero atoms of N, O or S; $R_4$ is selected from the group consisting of H,

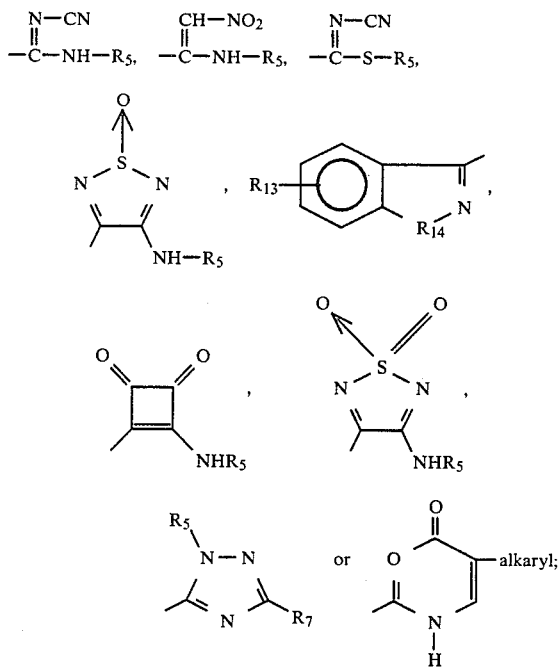

$R_5$ is H or lower alkyl;
$R_6$ is H or lower alkyl or $R_6$ together with $R_2$ are ethylene or propylene and form a 5 or 6 membered ring with the nitrogen atoms to which they are attached;
$R_7$ is hydrogen, lower alkyl, lower alkenyl, aryl, arloweralkyl, hydroxyloweralkyl, acyloxyloweralkyl, loweralkoxyloweralkyl, aryloxyalkyl, aroyloxyalkyl, aralkyloxyalkyl, aminoalkyl, alkylaminoalkyl, dialkylaminoalkyl, hydroxy, alkoxy, alkylthio, halogen or $NR_8R_9$, where:
$R_8$ is hydrogen, lower alkyl, lower alkenyl or arloweralkyl; and
$R_9$ is hydrogen, $COR_{10}$, $SO_2R_{11}$ or

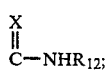

$R_{10}$ is hydrogen, lower alkyl, aryl, arloweralkyl, loweralkoxy, heteroaryl, or monocyclic heteroarylalkyl;
$R_{11}$ is loweralkyl or aryl;
$R_{12}$ is hydrogen, lower alkyl, cycloloweralkyl, aryl or lower aralkyl;
$R_{13}$ is halo, amino, nitro, cyano, hydroxy, lower alkyl, lower alkoxy, lower alkanoyl, cycloloweralkyl, mono- or di lower alkyl amino, lower alkanoyl, lower alkanoyl amino, haloloweralkyl, aryl, mercapto, loweralkoxy carbonyl, carboxy, loweralkylthio, loweralkylsulfonyl, sulfamoyl, or lower alkyl sulfamoyl; and
$R_{14}$ is $SO_2$, SO, S or C=O;
or a pharmaceutically acceptable salt thereof.

Compounds within the scope of Formula I exhibit physiological activity in mammals including anti-secretory activity, histamine $H_2$-receptor antagonist activity, anti-ulcer activity and cytoprotective activity.

Another aspect of this invention relates to the class of isomeric compounds according to Formula I, which class of compounds exhibits an unexpected and surprising level of physiological activity including anti-secretory, histamine $H_2$-receptor antagonist and anti-ulcer activity.

This invention also relates to methods for the treatment and prevention of gastrointestinal hyperacidity and ulcerogenic disorders in humans and other mammals comprising administering to a patient an effective amount of a compound within the description of Formula I.

DETAILED DESCRIPTION OF THE INVENTION

Preferred classes of compounds according to this invention are described by Formulae II, III, IV, V and VI.

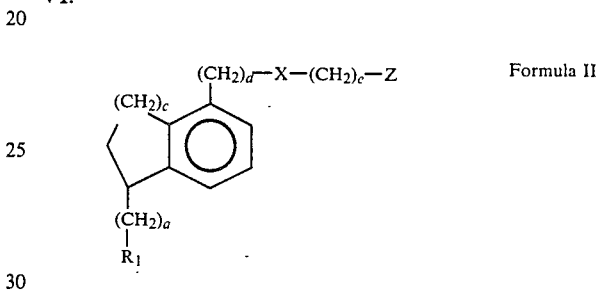

Formula II or;

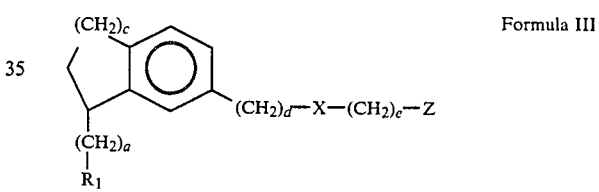

Formula III wherein:
a is 0, 1 or 2;
c is 0, 1, 2 or 3;
d is 0 or 1;
e is 2, 3 or 4;
X is oxygen or sulfur;
Z is $NHR_4$ or

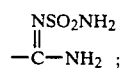

$R_1$ is $-NR_2R_3$;
$R_2$, $R_3$, $R_4$ and $R_5$ are as described above.

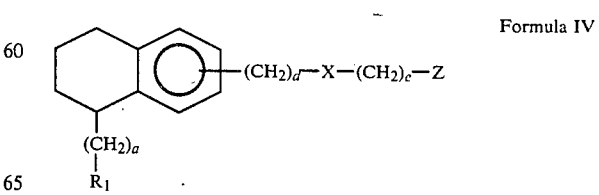

Formula IV or;

-continued

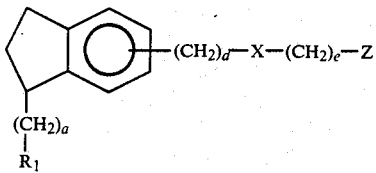

wherein:
a is 0, 1 or 2;
d is 0 or 1;
e is 2, 3 or 4;
X is oxygen or sulfur;
Z is $NHR_4$ or

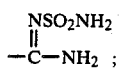

$R_1$ is $-NR_2R_3$;
$R_2$, $R_3$, $R_4$ and $R_5$ are as described above.

Formula VI

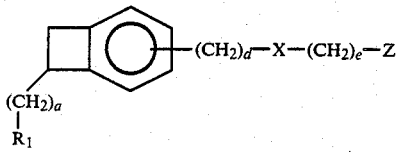

wherein:
a is 1 or 2;
d is 0 or 1;
e is 2, 3 or 4;
X is oxygen or sulfur;
Z is $NHR_4$ or

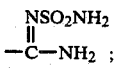

$R_1$ is $-NR_2R_3$;
$R_2$, $R_3$, $R_4$ and $R_5$ are as described above.

A most preferred class of compounds within the scope of Formula I comprises the compounds of Formula I wherein:
a is 0;
b is 0;
c is 0, 1, 2 or 3;
d is 0;
e is 3;
X is oxygen; and
Z is $NHR_4$ or

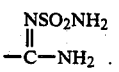

A preferred subclass of compounds is described by Formula IV or V, wherein:
a and d are 0;
e is 3; and
X is oxygen.

Another preferred subclass of compounds is described by Formula IV or V, wherein:
a is 0;
d is 1;
e is 2; and
X is sulfur.

A preferred Z substituent is selected from the group including

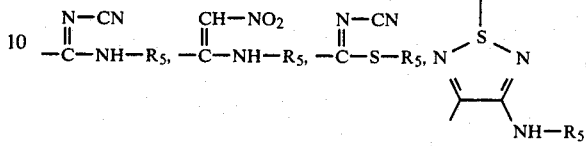

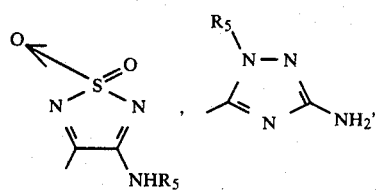

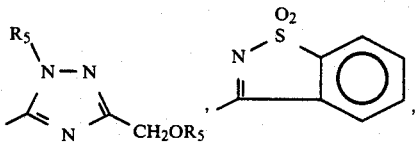

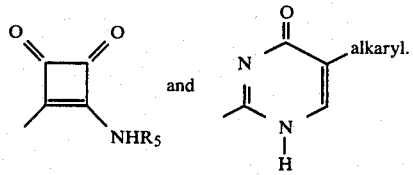

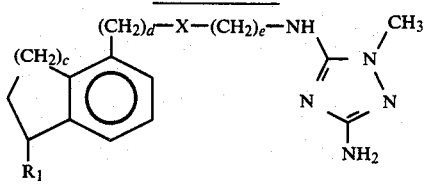

A most preferred class of compounds is described by Formula VII.

Formula VII

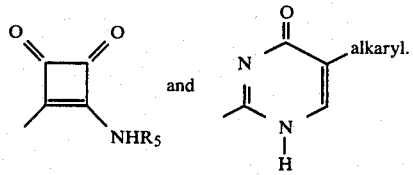

wherein:
c is 1 or 2;
d is 0 or 1;
e is 2, 3 or 4;
X is oxygen or sulfur;
$R_1$ is $-NR_2R_3$;
$R_2$ and $R_3$ together with the nitrogen to which they are attached form a 5, 6 or 7 membered heterocyclic ring which may include one to three additional hetero atoms of N, O or S;
or a pharmaceutically acceptable salt thereof.

A particularly interesting class of compounds according to Formula VII comprises those compounds wherein $R_1$ is 1-piperidinyl, 1-pyrrolidinyl, 1-morpholinyl or 1-azepinyl.

The compounds of Formulae I to VII may also form hydrates and exhibit tautomerism. Formulae I to VII are intended to encompass all hydrates and tautomers, as well as any diastereomers and optical enantiomers.

As employed above and throughout the disclosure, the following terms, unless otherwise indicated, shall be understood to have the following meanings:

"Lower alkyl" means an alkyl group as above, having 1 to about 4 carbon atoms. Examples of lower alkyl groups are methyl, ethyl, n-propyl, isopropyl, butyl, sec-butyl, and tert-butyl.

"5, 6 or 7 membered heterocyclic ring" means a nitrogen-containing ring of the formula

—N   Y where Y is alkylene or alkylidinyl having from one to six carbon atoms, and may include one to three atoms of N, O or S. Exemplary heterocyclic groups include piperidinyl, pyrrolidinyl, morpholinyl, azepinyl, pyrrolyl, imidazolyl, pyrazolyl, and thiamorpholinyl.

"Aroyl" means an acyl derivative of an aromatic carboxylic acid such as benzoyl and quinolyl.

"Heteroaryl" means a five or six membered monocyclic ring or 9 or 10 membered bicyclic ring either of which may contain one or more heteroatoms of nitrogen, oxygen or sulfur, including furyl, pyridyl, thiazolyl, quinolinyl, indolyl or thienyl.

"Lower alkanoyl" means an acyl derivative of a lower alkanoic acid such as acetyl and propionyl.

"Aryl" means an aromatic hydrocarbon radical group such as phenyl, toluyl, quinolyl, pyridyl, and includes phenyl, toluyl, quinolyl or pyridyl substituted by one or more substituent groups including lower alkyl, halo, carboxyl, amino, loweralkyl amino, amido, hydroxyl, nitro, cyano, or sulfonyl. Preferred aryl groups include phenyl and toluyl.

Representative examples of compounds of this invention are listed below in Tables A, B, C, D, E, F, G and H.

TABLE A-continued

| R₁ | Z |
|---|---|
| piperidin-1-yl | $-NH-C(=N-NH-)-NHCH_3$ (guanidine-hydrazone derivative) |
| piperidin-1-yl | $-CN$ |
| piperidin-1-yl | $-C(=NSO_2NH_2)-NH_2$ |
| piperidin-1-yl | $-NH_2$ |
| pyrrolidin-1-yl | $-CN$ |
| pyrrolidin-1-yl | $-C(=NSO_2NH_2)-NH_2$ |
| pyrrolidin-1-yl | $-NH_2$ |
| $-C(=NH)-N(CH_3)_2$ | 1-methyl-3-amino-5-(NH-)-1,2,4-triazole |
| $-C(=NH)-$(pyrrolidin-1-yl) | 1-methyl-3-amino-5-(NH-)-1,2,4-triazole |
| $-C(=NH)-NHCH_3$ | 1-methyl-3-amino-5-(NH-)-1,2,4-triazole |
| $-C(=NH)-N(CH_3)_2$ | 3-NH-4-NHCH₃-1,2,5-thiadiazole 1-oxide |
| $-C(=NH)-$(pyrrolidin-1-yl) | 3-NH-4-NHCH₃-1,2,5-thiadiazole 1-oxide |
| $-C(=NH)-NHCH_3$ (H on N) | 3-NH-4-NHCH₃-1,2,5-thiadiazole 1-oxide |
| piperidin-1-yl | 1-methyl-3-amino-5-(NH-)-1,2,4-triazole |

TABLE B

Structure: tetrahydronaphthalene with R₁ substituent and $-OCH_2CH_2CH_2Z$ substituent

| R₁ | Z |
|---|---|
| $-N(CH_3)_2$ | $-NH-C(=NCN)-NHCH_3$ |
| $-N(CH_3)_2$ | $-NH-C(=CHNO_2)-NHCH_3$ |
| piperidin-1-yl | 1-methyl-3-amino-5-(NH-)-1,2,4-triazole |
| pyrrolidin-1-yl | $-NH-C(=N-)-NH-$ pyrimidinone with methylenedioxyphenyl-CH₂ |
| morpholin-4-yl | $-NH-C(=N-)-NH-$ pyrimidinone with (6-methylpyridin-3-yl)-CH₂ |

TABLE B-continued

[Structure: tetrahydronaphthalene with R₁ and OCH₂CH₂CH₂Z substituents]

| R₁ | Z |
|---|---|
| —NH₂ | —NH, NH₂ on thiadiazole S-oxide |
| —NHCH₃ | —NH, NH₂ on thiadiazole S,S-dioxide |
| —N(CH₃)₂ | —NH, NH₂ on thiadiazole S,S-dioxide |
| —N(CH₃)₂ | —NH, NHCH₃ on thiadiazole S-oxide |
| —N(CH₃)₂ | pyrimidinone-CH₂-(6-methylpyridin-3-yl) |
| —N(Et)₂ | pyrimidinone-CH₂-(benzo[d][1,3]dioxol-5-yl) |
| —N(Et)₂ | methyl-triazole with —NH and —NHCH₃ substituents |
| —NHEt | —NH—C(=CHNO₂)—NH₂ |

TABLE B-continued

[Structure: tetrahydronaphthalene with R₁ and OCH₂CH₂CH₂Z substituents]

| R₁ | Z |
|---|---|
| —NHCH₃ | —NH—C(=NCN)—SCH₃ |
| piperidino | —NH—C(=NCN)—NHCH₃ |

TABLE C

[Structure: indane with R₁ and CH₂SCH₂CH₂Z substituents]

| R₁ | Z |
|---|---|
| —NH₂ | —NH—C(=NCN)—NHCH₃ |
| —N(CH₃)₂ | —NH—C(=NCN)—NH₂ |
| —NHCH₃ | —NH—C(=CHNO₂)—NHCH₃ |
| piperidino | —NH—C(=CHNO₂)—NH₂ |
| pyrrolidino | —NH—C(=NCN)—S—CH₃ |
| —NHCH₃ | pyrimidinone-CH₂-(benzo[d][1,3]dioxol-5-yl) |
| piperidino | pyrimidinone-CH₂-(6-methylpyridin-3-yl) |
| —N(CH₃)₂ | —NH, NH₂ on thiadiazole S-oxide |

TABLE C-continued

Structure: indane with CH₂SCH₂CH₂Z substituent on benzene ring and R₁ on the saturated ring.

| R₁ | Z |
|---|---|
| pyrrolidin-1-yl | —NH–C(=N–S(=O)–N)–NHCH₃ (4-methylamino-1,2,5-thiadiazol-3-ylamino 1-oxide) |
| piperidin-1-yl | 1-methyl-3-amino-1,2,4-triazol-5-yl-NH— |
| morpholin-4-yl | 1-ethyl-3-(methylamino)-1,2,4-triazol-5-yl-NH— |
| hexahydroazepin-1-yl | 1H-3-(methylamino)-1,2,4-triazol-5-yl-NH— |
| piperidin-1-yl | 1-ethyl-3-(methylamino)-1,2,4-triazol-5-yl-NH— |
| pyrrolidin-1-yl | 1H-3-(methylamino)-1,2,4-triazol-5-yl-NH— |
| —N(CH₃)₂ | 1-ethyl-3-(methylamino)-1,2,4-triazol-5-yl-NH— |
| —C(=NH)NH₂ | 1H-3-(methylamino)-1,2,4-triazol-5-yl-NH— |

TABLE D

Structure: indane with OCH₂CH₂CH₂Z substituent on benzene ring and R₁ on the saturated ring.

| R₁ | Z |
|---|---|
| —N(CH₃)₂ | —NH–C(=NCN)–NHCH₃ |
| pyrrolidin-1-yl | —NH–C(=CHNO₂)–NHCH₃ |
| piperidin-1-yl | 1-methyl-3-amino-1,2,4-triazol-5-yl-NH— |
| morpholin-4-yl | 5-(benzo[1,3]dioxol-5-ylmethyl)-6-oxo-1,6-dihydropyrimidin-2-yl-NH— |
| —C(=NH)NH₂ | 5-[(6-methylpyridin-3-yl)methyl]-6-oxo-1,6-dihydropyrimidin-2-yl-NH— |
| —N(CH₃)₂ | 1-methyl-3-amino-1,2,4-triazol-5-yl-NH— |
| —NH₂ | 4-amino-1,2,5-thiadiazol-3-yl-NH— 1-oxide |
| piperidin-1-yl | 4-amino-1,2,5-thiadiazol-3-yl-NH— 1,1-dioxide |

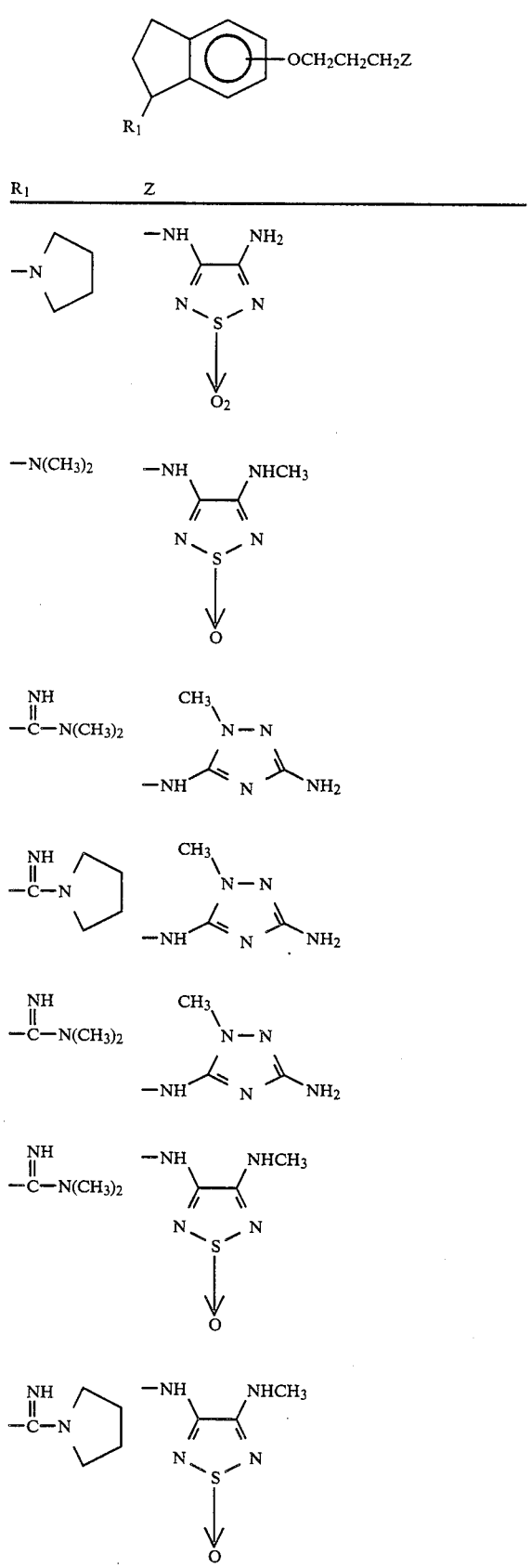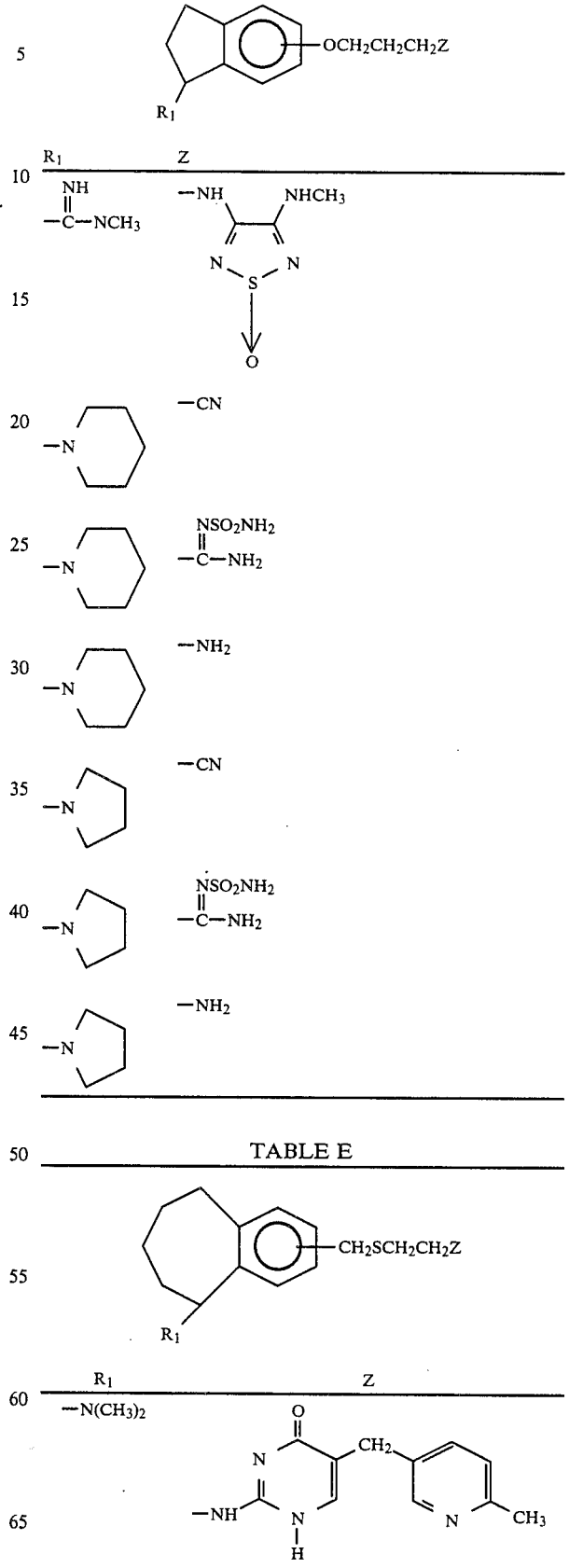

TABLE E-continued

[Structure: bicyclic system with R₁ and CH₂SCH₂CH₂Z substituents]

| R₁ | Z |
|---|---|
| —N(Et)₂ | [pyrimidinone-methylenedioxyphenyl structure] |
| —N(piperidine) | [1-methyl-triazole with NH and NHCH₃ substituents] |
| —N(piperidine) | —NH—C(=CHNO₂)—NH₂ |
| —N(morpholine) | —NH—C(=NCN)—SCH₃ |
| —N(piperidine) | —NH—C(=N—CN)—NHCH₃ |

TABLE F

[Structure: tetrahydronaphthalene with R₁ and CH₂SCH₂CH₂Z substituents]

| R₁ | Z |
|---|---|
| —N(piperidine) | —CN |
| —N(piperidine) | —C(=NSO₂NH₂)—NH₂ |
| —N(piperidine) | —NH₂ |
| —N(pyrrolidine) | —CN |

TABLE F-continued

[Structure: tetrahydronaphthalene with R₁ and CH₂SCH₂CH₂Z substituents]

| R₁ | Z |
|---|---|
| —N(pyrrolidine) | —C(=NSO₂NH₂)—NH₂ |
| —N(pyrrolidine) | —NH₂ |

TABLE G

[Structure: indane with (CH₂)ₐ-piperidine and O-(CH₂)ₑ-NH-R₄ substituents]

| a | e | R₄ |
|---|---|---|
| 0 | 3 | [1-methyl-triazole with NHC(=O)CH₃] |
| 0 | 3 | [1-methyl-triazole with CH₂OCH₃] |
| 0 | 3 | [1-methyl-triazole with CH₂—O—C(=O)—CH₃] |
| 0 | 3 | [cyclobutenedione with methyl and NHCH₃] |
| 0 | 3 | [cyclobutenedione with methyl and NH—C(=O)—CH₃] |
| 1 | 3 | [1-methyl-pyrazole with CH₂OH] |

TABLE G-continued

[Structure: indane with piperidinyl-(CH2)a substituent and O-(CH2)e-NH-R4 substituent]

| a | e | R4 |
|---|---|---|
| 1 | 3 | 1-methyl-5-methyl-3-(CH2OCH3)-1,2,4-triazole |
| 1 | 3 | 1-methyl-5-methyl-3-(CH2-O-C(=O)-CH3)-1,2,4-triazole |
| 1 | 3 | 1-methyl-5-methyl-3-(NH2)-1,2,4-triazole |
| 1 | 3 | 1-methyl-5-methyl-3-(NHCH3)-1,2,4-triazole |
| 1 | 3 | 3-methyl-4-(NHCH3)-cyclobutene-1,2-dione |
| 1 | 3 | 3-methyl-4-(NH2)-cyclobutene-1,2-dione |
| 1 | 3 | 3-methyl-4-(NHC(=O)CH3)-cyclobutene-1,2-dione |
| 1 | 3 | benzisothiazole-1,1-dioxide |
| 0 | 4 | 1-methyl-5-methyl-3-(NHC(=O)CH3)-1,2,4-triazole |

TABLE G-continued

[Structure: indane with piperidinyl-(CH2)a substituent and O-(CH2)e-NH-R4 substituent]

| a | e | R4 |
|---|---|---|
| 0 | 4 | 1-methyl-5-methyl-3-(CH2OCH3)-1,2,4-triazole |
| 0 | 4 | 1-methyl-5-methyl-3-(CH2-O-C(=O)-CH3)-1,2,4-triazole |
| 0 | 4 | 3-methyl-4-(NHCH3)-cyclobutene-1,2-dione |
| 0 | 4 | 3-methyl-4-(NHC(=O)CH3)-cyclobutene-1,2-dione |
| 1 | 4 | 1-methyl-5-methyl-3-(CH2OH)-1,2,4-triazole |
| 1 | 4 | 1-methyl-5-methyl-3-(CH2OCH3)-1,2,4-triazole |
| 1 | 4 | 1-methyl-5-methyl-3-(CH2-O-C(=O)-CH3)-1,2,4-triazole |
| 1 | 4 | 1-methyl-5-methyl-3-(NH2)-1,2,4-triazole |
| 1 | 4 | 1-methyl-5-methyl-3-(NHCH3)-1,2,4-triazole |
| 1 | 4 | 3-methyl-4-(NHCH3)-cyclobutene-1,2-dione |

TABLE G-continued

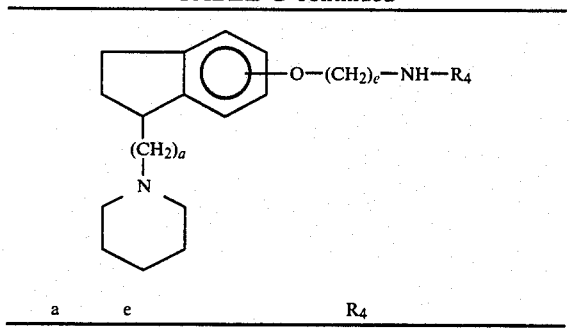

| a | e | R₄ |
|---|---|---|
| 1 | 4 | 3-amino-4-methyl-cyclobutene-1,2-dione |
| 1 | 4 | 3-(N-acetylamino)-4-methyl-cyclobutene-1,2-dione |
| 1 | 4 | 3-methyl-benzisothiazole-1,1-dioxide |
| 0 | 3 | 4-methyl-3-(methylamino)-1,2,5-thiadiazole 1-oxide |
| 0 | 3 | 4-methyl-3-(acetylamino)-1,2,5-thiadiazole 1-oxide |
| 0 | 4 | 3-amino-4-methyl-1,2,5-thiadiazole 1-oxide |
| 0 | 4 | 4-methyl-3-(methylamino)-1,2,5-thiadiazole 1-oxide |
| 0 | 4 | 4-methyl-3-(acetylamino)-1,2,5-thiadiazole 1-oxide |
| 1 | 3 | 3-amino-4-methyl-1,2,5-thiadiazole 1-oxide |
| 1 | 3 | 4-methyl-3-(methylamino)-1,2,5-thiadiazole 1-oxide |
| 1 | 3 | 4-methyl-3-(acetylamino)-1,2,5-thiadiazole 1-oxide |
| 1 | 4 | 3-amino-4-methyl-1,2,5-thiadiazole 1-oxide |
| 1 | 4 | 4-methyl-3-(methylamino)-1,2,5-thiadiazole 1-oxide |
| 1 | 4 | 4-methyl-3-(acetylamino)-1,2,5-thiadiazole 1-oxide |

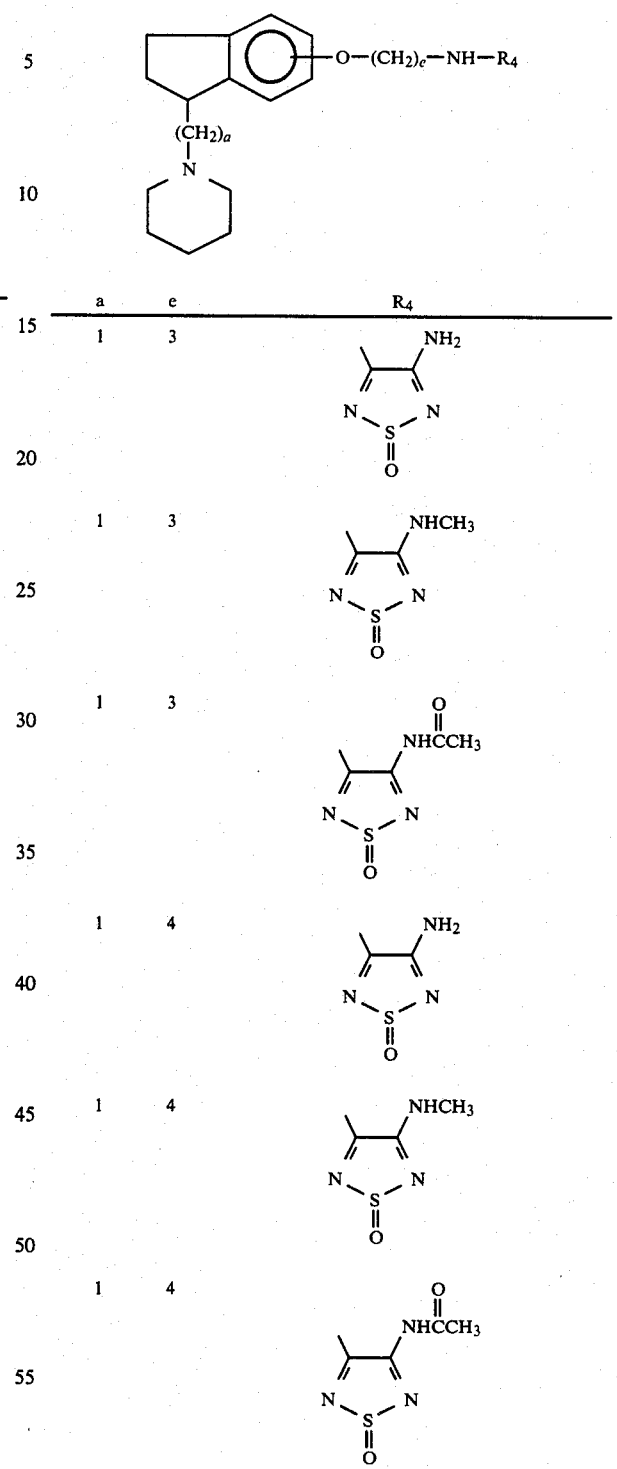

TABLE H

[Structure: benzocyclobutene with CH₂-N-piperidine (CH₂)ₐ substituent and O-(CH₂)ₑ-NH-R₄ substituent]

| a | e | R₄ |
|---|---|---|
| 0 | 3 | 1-methyl-1,2,4-triazole with C(=N)CH₃ and C(=N)NHCOCH₃ |
| 0 | 3 | 1-methyl-1,2,4-triazole with C(=N)CH₃ and C(=N)CH₂OCH₃ |
| 0 | 3 | 1-methyl-1,2,4-triazole with C(=N)CH₃ and C(=N)CH₂-O-C(=O)CH₃ |
| 0 | 3 | cyclobutenedione with CH₃ and NHCH₃ |
| 0 | 3 | cyclobutenedione with CH₃ and NHCOCH₃ |
| 1 | 3 | 1-methyl-1,2,4-triazole with C(=N)CH₃ and C(=N)CH₂OH |
| 1 | 3 | 1-methyl-1,2,4-triazole with C(=N)CH₃ and C(=N)CH₂OCH₃ |
| 1 | 3 | 1-methyl-1,2,4-triazole with C(=N)CH₃ and C(=N)CH₂-O-C(=O)CH₃ |
| 1 | 3 | 1-methyl-1,2,4-triazole with C(=N)CH₃ and C(=N)NH₂ |
| 1 | 3 | 1-methyl-1,2,4-triazole with C(=N)CH₃ and C(=N)NHCH₃ |
| 1 | 3 | cyclobutenedione with CH₃ and NHCH₃ |
| 1 | 3 | cyclobutenedione with CH₃ and NH₂ |
| 1 | 3 | cyclobutenedione with CH₃ and NHCOCH₃ |
| 1 | 3 | benzisothiazole-S,S-dioxide with CH₃ |
| 0 | 4 | 1-methyl-1,2,4-triazole with C(=N)CH₃ and C(=N)NHCOCH₃ |
| 0 | 4 | 1-methyl-1,2,4-triazole with C(=N)CH₃ and C(=N)CH₂OCH₃ |
| 0 | 4 | 1-methyl-1,2,4-triazole with C(=N)CH₃ and C(=N)CH₂-O-C(=O)CH₃ |
| 0 | 4 | cyclobutenedione with CH₃ and NHCH₃ |
| 0 | 4 | cyclobutenedione with CH₃ and NHCOCH₃ |
| 1 | 4 | 1-methyl-1,2,4-triazole with C(=N)CH₃ and C(=N)CH₂OH |
| 1 | 4 | 1-methyl-1,2,4-triazole with C(=N)CH₃ and C(=N)CH₂OCH₃ |

TABLE H-continued
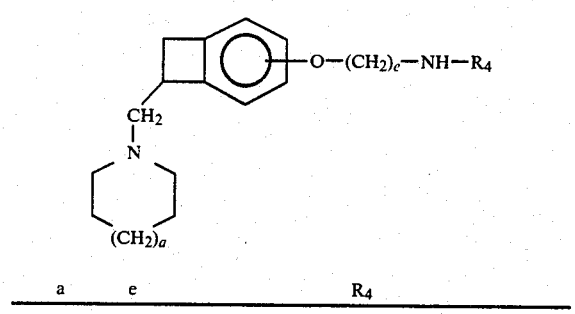
| a | e | R4 |
|---|---|---|
| 1 | 4 | 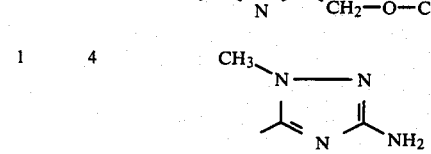 |
| 1 | 4 | 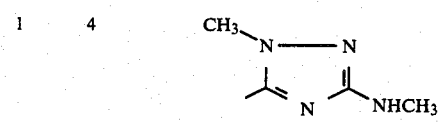 |
| 1 | 4 | 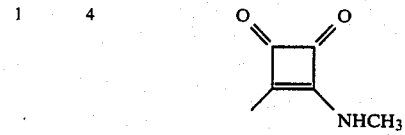 |
| 1 | 4 | 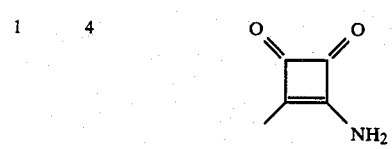 |
| 1 | 4 | 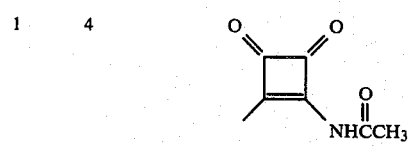 |
| 1 | 4 | 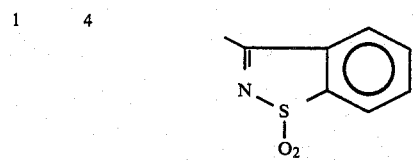 |
| 1 | 4 | 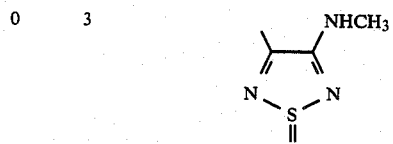 |
| 0 | 3 | 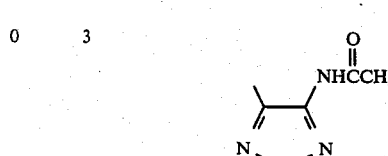 |
| 0 | 3 |  |
TABLE H-continued
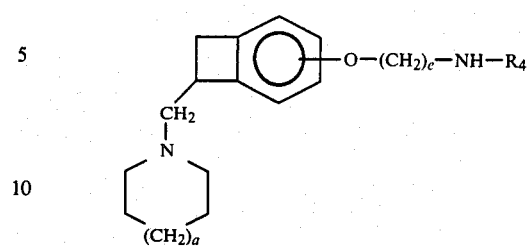
| a | e | R4 |
|---|---|---|
| 0 | 4 |  |
| 0 | 4 |  |
| 0 | 4 | 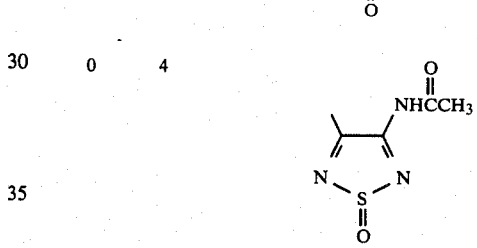 |
| 1 | 3 | 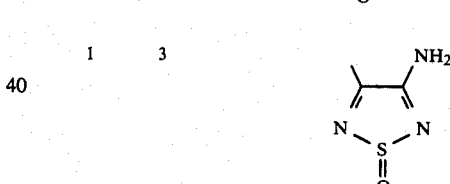 |
| 1 | 3 | 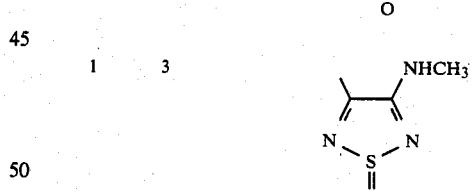 |
| 1 | 3 | 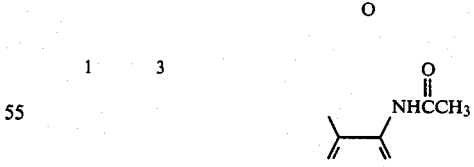 |
| 1 | 4 | 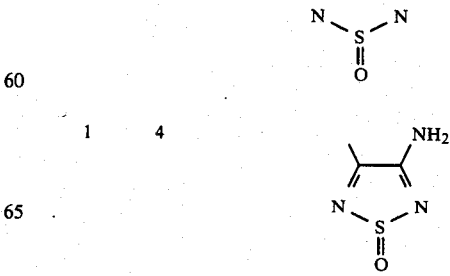 |

TABLE H-continued

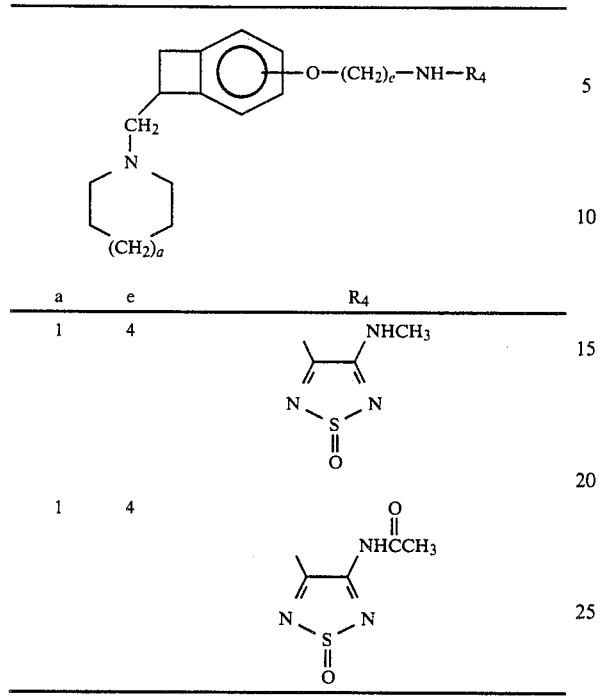

| a | e | R$_4$ |
|---|---|---|
| 1 | 4 | (structure with NHCH$_3$, N-S(=O)-N ring with methyl) |
| 1 | 4 | (structure with NHC(=O)CH$_3$, N-S(=O)-N ring with methyl) |

The compounds of this invention may be prepared by one of the following general synthetic schemes.

When the bicyclic benzenoid portion of the compound is directly attached to the X component of Formula I, these compounds may be prepared from a bicyclic phenolic (or phenylmercaptan) intermediate shown by Formula VIII below.

One means of obtaining the appropriately substituted phenolic (or thiol) intermediate of Formula VIII is illustrated in Scheme I. The starting material may be a bicyclic ketone having an oxy or mercaptyl substituent in any one of the four positions possible on the phenyl ring. The ketone can either be obtained from a commercially available source or prepared according to standard procedures known in the art.

The ketone is then converted to the enamine using a primary or secondary amine in the presence of acid, preferably a Lewis acid such as titanium tetrachloride. Any polar aprotic solvent may be used in this reaction, for example, toluene or methylene chloride.

The resulting enamine is reduced, preferably using a hydride reagent such as a borohydride. Sodium cyanoborohydride is one preferred reducing agent.

The phenolic protecting group is then cleaved to obtain the intermediate of Formula VIII.

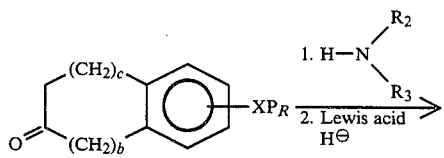

Scheme I

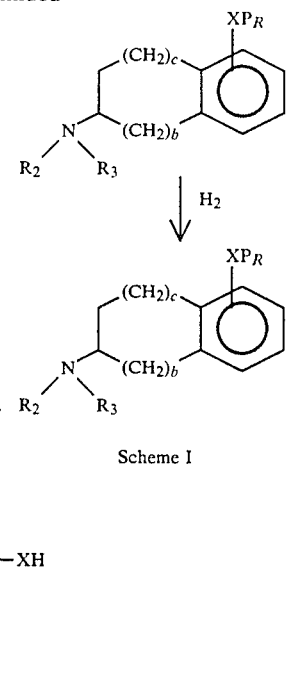

VIII

The protecting group, P$_R$, may be methyl, benzyl or the N-phthalimido alkyl. If the protecting group is chosen to be other than the N-phthalimido alkyl, the protecting group is removed according to methods known in the art. If the protecting group is N-phthalimido alkyl, then it can remain on the synthetic intermediate preceding VIII and used as in the subsequent reaction step.

The formation of the ether linkage from VIII is accomplished by treating the phenolic compound with a protected N-propylbromide in the presence of a base such as sodium methoxide, potassium t-butoxide or potassium carbonate. Ether coupling reagents other than a base and a bromide may also be used. (Scheme II)

Scheme II

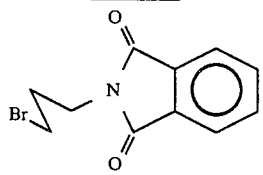

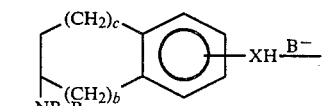

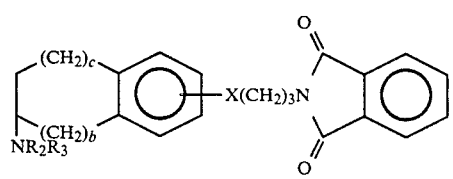

The nitrogen protecting group is preferably phthalimido but can be any protecting group insensitive to the ether formation reaction conditions, such as a base insensitive group.

The amine compound is obtained by the removal of the protecting group, for example, the phthalimido group is removed with hydrazine hydrate. (Scheme III)

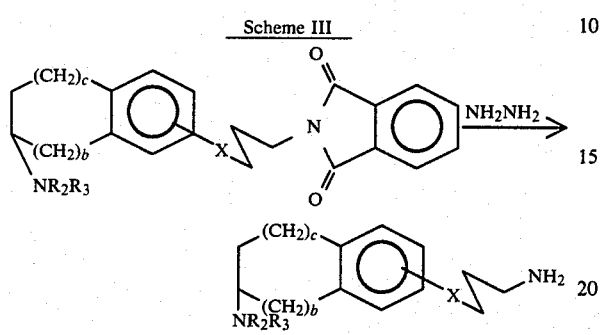

An alternate route to compounds of Formula VIII above involves the reduction of the ketonic phenol, followed by the halogenation of the resulting hydroxy compound and the substitution of the desired amino group for the halo group. Scheme IV below depicts this reaction sequence showing exemplary reagents to effect the desired reactions.

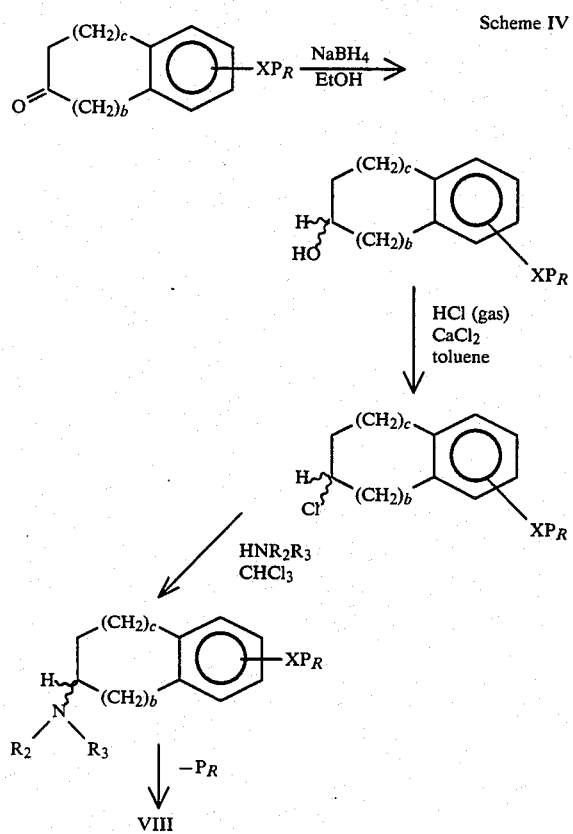

An alternate route for the formation of the ether linkage from VIII involves the base catalyzed reaction of the phenolic compound with an α,ω-dihaloalkyl reagent followed by the nucleophilic displacement of the ω-halo substitutent by azide and the reduction of the azido function to the amine. Scheme V depicts the alternate "azide" route.

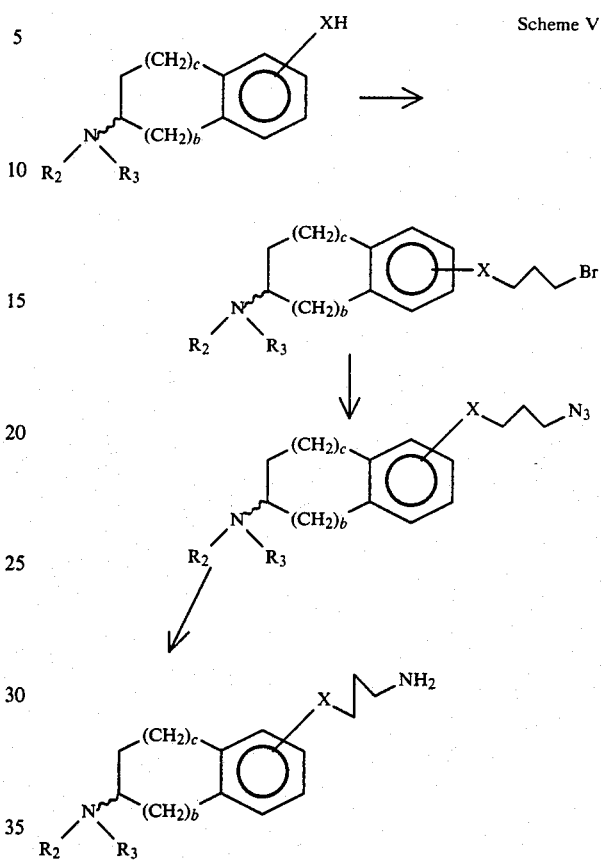

Compounds within the scope of Formula I and having a methyleneoxy or methylenethioxy substituent (d=1)on the phenyl portion of the compound may be prepared by one of the reaction sequences described below.

The methyleneoxy or methylenethio ether may be prepared from the coupling of a 2-bromoethylene phthalimide in the presence of base or 2-thioethylamine, respectively, with the methylene hydroxy compound. Scheme VI illustrates the formation of the methylenethio ether.

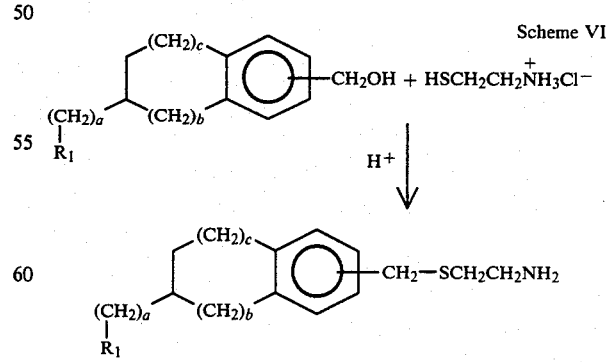

The methyleneoxy compound may be obtained by the reduction of a phenyl carboxylic acid or ester precursor such as IX. The reduction may be conducted by hydrogenation over a rhenium catalyst, by a hydride in the presence of a Lewis acid or by acidic electrolysis and depending on choice of conditions may take place before or after the formation of the amine.

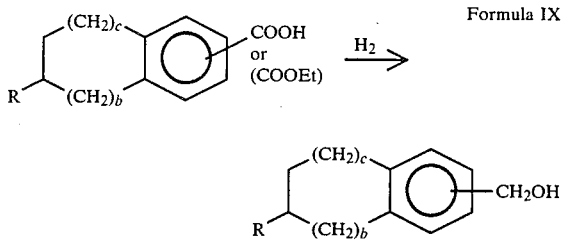

Formula IX

If the reduction to the methylene hydroxy compound occurs after the formation of the amine, the carboxylic acid intermediate is prepared analogously to the phenolic intermediate VIII, with the acid being protected by its ester where appropriate.

Compounds within the scope of Formula I, where a is greater than zero, may be prepared by the addition of one or more carbon units at the keto- position of the starting bicyclic ketone compound as shown in Scheme VII.

*Synth. Commun.* 12, No. 10, 763–70 (1982)). An alternative pathway to the carboxylic acid compound which also provides a pathway to amido and amidino derivatives is effected by the use of tosylmethylisocyanide in the presence of base. For a complete discussion of the one-step conversion of the ketone to the cyano derivative, see O. H. Oldenziel et al, J. Org. Chem., Vol. 42, No. 19, 3114–3117 (1977). The most preferred base is tert-butoxide in a non-polar aprotic solvent such as dimethylsulfoxide or HMPT. The resulting cyano compound may be hydrolyzed to the acid by means of aqueous base, for example, aqueous sodium hydroxide, or it may be hydrolyzed to the carbamoyl derivative by acidic means including, for example, $BF_3$ in glacial acetic acid or aqueous hydrochloric acid.

The mono- or di-substituted amide may be formed by the reaction of the acyl chloride, prepared by treating the acid with $SOCl_2$ with a primary or secondary amine, i.e., $HNR_2R_3$. The amide may also be formed directly by a condensation reaction of the acid and amine or through the ester by amide-ester interchange.

Reduction of the amide results in the methylene amine. A hydride reducing agent such as $LiAlH_4$ in diethyl ether or tetrahydrofuran is preferred. Other reagents which may be used include $LiAlH_4$ and $AlCl_3$ Scheme VII

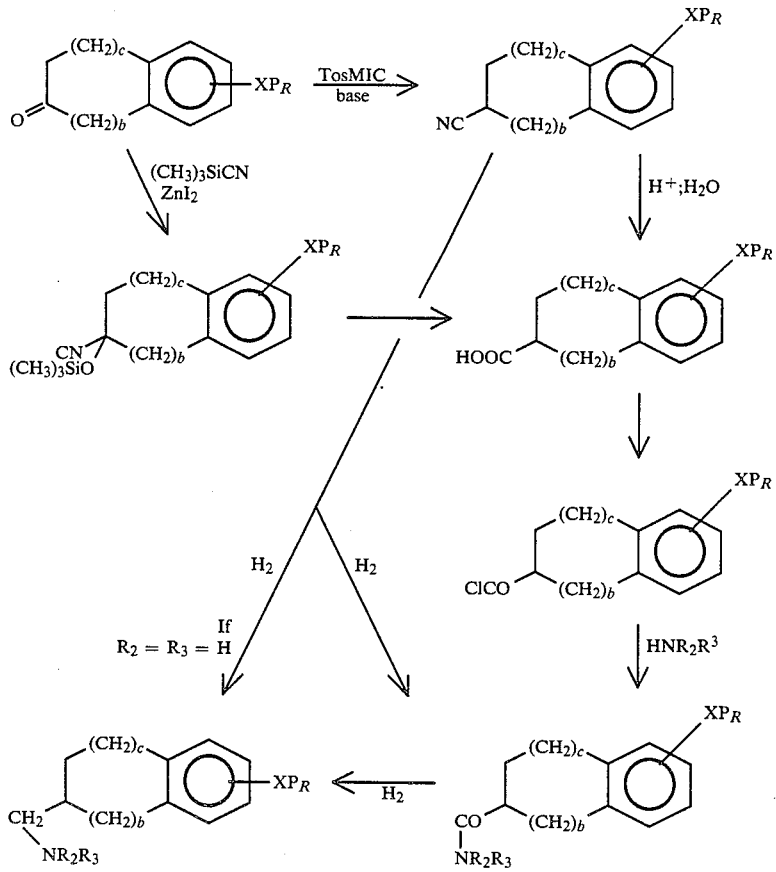

Treatment of the bicylic ketone with trimethylsilylcyanide and zinc iodide forms the cyano trimethylsiloxy adduct in good yield. Treatment of the siloxy compound with a mixture of a Lewis acid such as tin$^{II}$ chloride and a concentrated halogenic acid such as conc. HCl in glacial acetic acid results in the formation of the carboxylic acid derivative. (See, J. L. Belletire et al, in an ether solvent, boron tetrafluoride etherate in methylene chloride followed by sodium borohydride in ethanol, and diborane in tetrahydrofuran. These reagents may also be used to obtain the amine directly from the cyano intermediate. The preferred reagent is LiAlH4.

The amine obtained from the reduction of the nitrile may be alkylated to form the mono-, di- or cyclized derivative using the appropriate alkylating agent, such as an alkyl iodide, alkyl triflate or 1,4-dihalo-, 1,5-dihalo-, or 1,6-dihalo-alkl compound. The pyrrolidinyl, 1-piperidinyl, morpholinyl and azepinyl compounds may be prepared by alkyating the amine with the appropriate reagents, for example, 1,4-dibromobutane or 1,5-dibromopentane.

The amidino derivatives may be prepared from the cyano intermediate. Treatment with anhydrous ethanolic hydrochloric acid forms the ethoxy iminium salt which forms the amidine upon treatment with a primary or secondary amine as depicted in Scheme VIII.

pound is generated by treatment of the halo derivative with a cyanide and either can be converted into the amide, amine or guanidine as described above, or the chain extension process can be continued by conversion via the carboxylic acid.

Another process for the preparation of compounds within Formula I wherein a is greater than zero, comprises the formation of spiro cyclic ether intermediate by the reaction of an alkylidinyl reagent with a cyclic ketone starting material. See Scheme X, below. Rupture of the oxygen containing ring is effected with a nucleophilic nitrogen reagent H—NR$_2$R$_3$. The tertiary hydroxy group is removed via dehydration. Hydrogenation of the unsaturated product is followed by elabora-

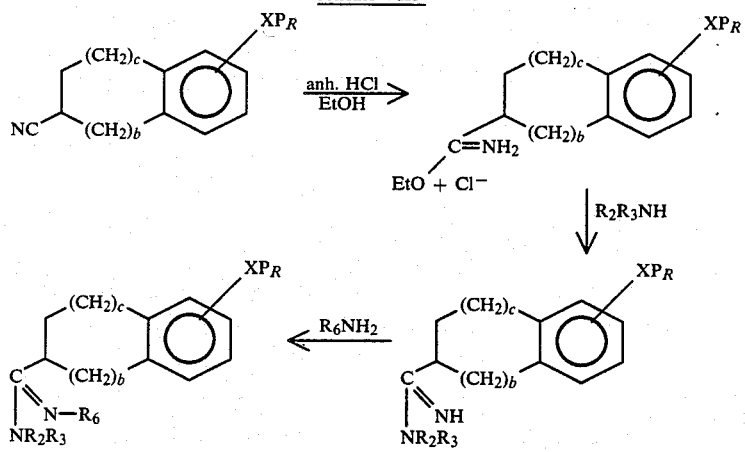

Scheme VIII

The ethylene amino and higher alkylene amino compounds according to Formula I may be prepared via the carboxylic acid intermediate by one or more alkylene chain extending reactions as shown, for example, in Scheme IX.

tion of the phenolic side chain as discussed herein above.

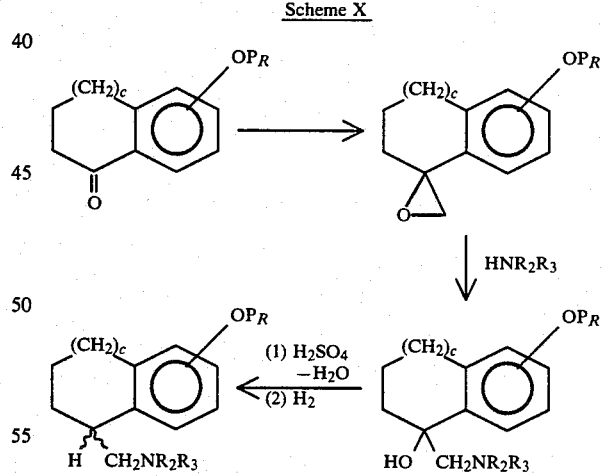

Scheme IX

X is Cl or Br

Reduction of the carboxylic acid, shown in Scheme IX, with a hydride such as diborane is followed by the conversion of the resultant hydroxy compound into the halo derivative with a halogenation reagent such as either SOCl$_2$ or PBr$_3$. The chain-extended cyano com- Compounds within the scope of Formula VI (b=c=O) are referred to as benzocyclobutenes and may be prepared according to the following reaction sequences.

3-Substituted benzocyclobutenes may be prepared starting from a 4-substitued indanone by means of a ring contraction reaction effected by photolysis of the appropriately substituted diazoindanone. The ring contraction reaction produced a 1-carboxylic acid benzocyclobutene which is converted to the 1-aminomethylene compound by reduction to the alcohol followed by the formation and displacement of an appropriate leaving group by the desired nucleophilic amine. Scheme XI below depicts an exemplary reaction sequence.

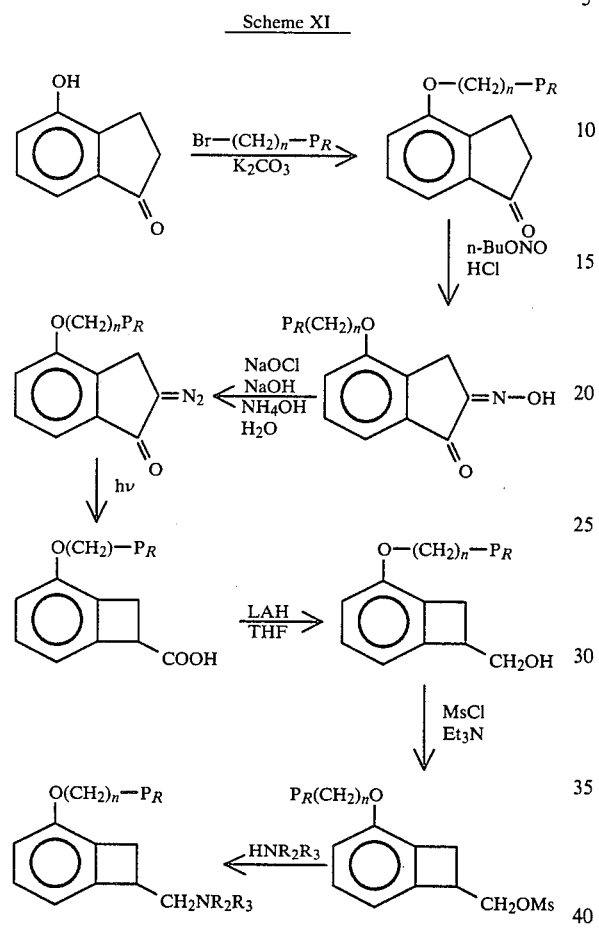

The Pr group designated in Scheme XI may be any protecting group which can be subsequently converted into an amino group by means known to persons skilled in the art.

5-substituted benzocyclobutenes may be prepared starting from a para-alkoxy benzaldehyde which is transformed by condensation with cyanoacetic acid, followed by hydrogenation, decarboxylation and bromination to yield a β-(4-alkoxy-3-bromophenyl)propionitrile. The bromo compound is cyclized to the benzocyclobutene and converted to the 1-aminomethylene benzocyclobutene by reactions described herein above. Scheme XII below depicts an exemplary sequence.

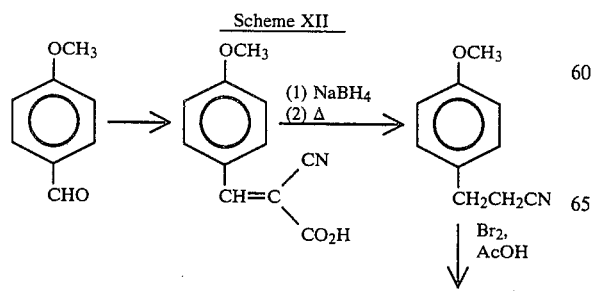

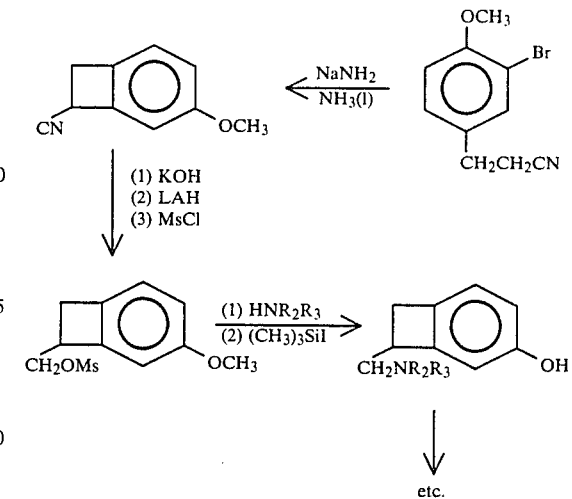

The addition of the terminal R$_4$ group comprises treating the amine with an R$_4$ end group precursor unit including those groups listed in Scheme XIII. The preparation of the precursors of the R$_4$ groups and the reaction conditions under which they are coupled to the primary amine are fully described in U.S. Pat. Nos. 4,104,381, 4,279,819, 4,323,566, 4,390,701, 4,395,553, and GB No. 2047238A, GB No. 2067987A, and EPO Publication No. 0081955A2, hereby incorporated by reference.

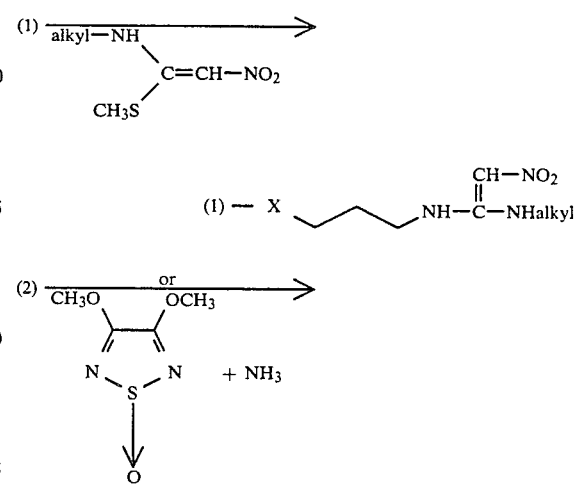

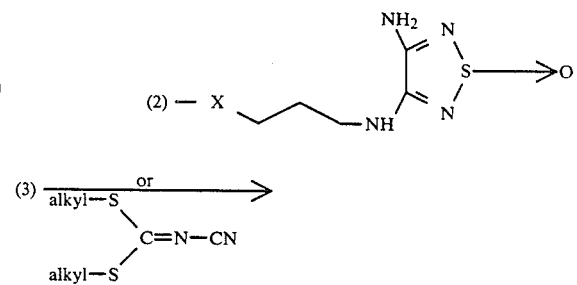

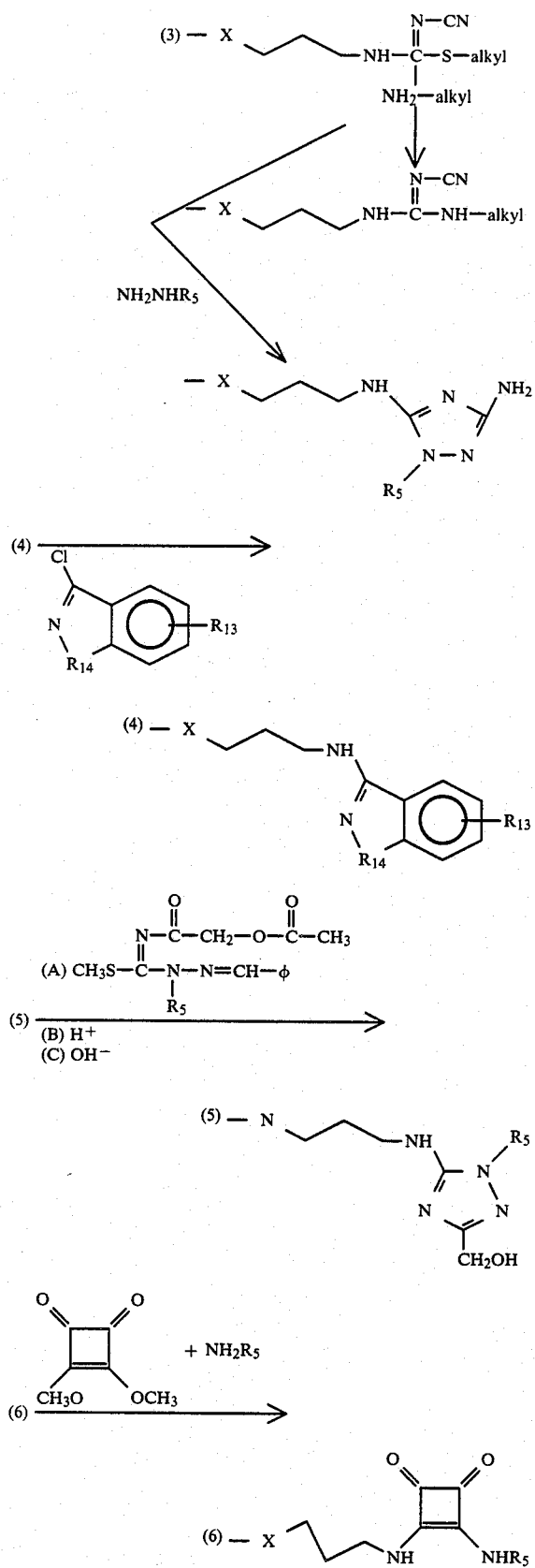

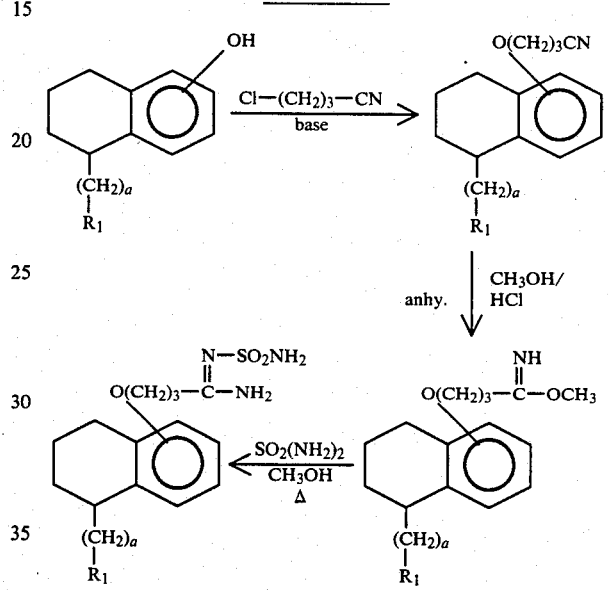

Scheme XIV. Reaction of the phenolic intermediate with a cyano-substituted alkylating agent such as 3-cyanopropylchloride in the presence of a base produces the cyano ether compound. Reduction of the cyano group with a hydride such as lithium aluminum hydride results in the amino compound. Treatment of the cyano compound with anhydrous methanolic HCl yields an imidate intermediate which is converted to the sulfonyl amidine by treatment with a sulfamide in methanol. For a complete discussion of this preparatory sequence, see U.S. Pat. No. 4,283,408, incorporated herein by reference.

The analogous mercaptan compounds may be prepared by reacting a cyano mercaptan with the appropriate halomethylene intermediate as shown in Scheme XV below. The amino sulfonyl amidine compound is prepared by reaction sequences similar to those described above.

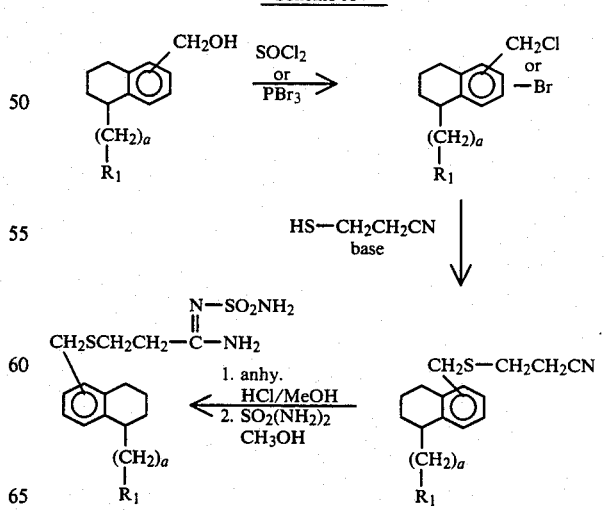

When Z is NH$_2$, CN or sulfamoyl amidine, the reaction sequence is slightly modified as shown below in The compounds of this invention may be readily converted to their non-toxic acid addition salts by customary methods in the art. The non-toxic salts of this invention are those salts the acid component of which is pharmacologically acceptable in the intended dosages, including those prepared from inorganic acids such as hydrochloric acid, hydrobromic acid, sulfuric acid, nitric acid and phosphoric acid, and from organic acids such as methane sulfonic acid, benzenesulfonic acid, acetic acid, propionic acid, malic acid, oxalic acid, succinic acid, glycolic acid, lactic acid, salicyclic acid, benzoic acid, nicotinic acid, phtalic acid, stearic acid, oleic acid, abietic acid, etc.

The following are selected examples of the preparation of the compounds according to this invention.

EXAMPLE 1

Preparation of 3-amino-4-[3-[7-(1-dimethylamino-1,2,3,4-tetrahydronaphthyloxy)]propylamino]-1,2,5-thiadiazole-1-oxide Step 1. 7-(3-Phthalimidopropoxy)-tetralone.

7-Hydroxy-1-tetralone (33.3 g) is dissolved in dimethylformamide (325 ml) and the mixture is cooled in an ice bath. Sodium methoxide (11.07 g) is added to the mixture. After the mixture is stirred for 3 min., N-(3-bromopropyl) phthalimide (54.96 g) is added to the mixture; stirring is continued and the reaction mixture stirred overnight. The resulting mixture is poured into $H_2O$ (650 ml), stirred for 1 hour, filtered, washed with $H_2O$ and air dried. The resulting fluffy nearwhite solid (62.8 g) is crystallized from ethyl acetate to give the desired product, a fluffy white solid (M.P. 149°–150° C.)

Step 2. 1-Dimethylamino-7-(3-phthalimido) propoxy-3,4-dihydronaphthalene.

A solution of titanium tetrachloride (5.4 g) in toluene (20 ml) is added over a period of 15 minutes to a stirred solution of 7-(3-phthalimido) propoxy-1-tetralone (19.9 g) suspended in a solution of anhydrous dimethyl amine (22 g) in dry toluene (200 ml) while maintaining a reaction temperature of about 1° C. under a $N_2$ atmosphere. When the addition is complete, the reaction mixture is allowed to warm to RT and stirred at RT for 4½ hours. The reaction mixture is filtered, the salts washed with dry toluene and the clear filtrate evaporated, affording a light yellow oil, which is stored under $N_2$ and used in the next step without any further treatment.

Step 3. 1-Dimethylamino-7-(3-phthalimido) propoxy-1,2,3,4-tetrahydronaphthalene.

Anhydrous hydrogen chloride gas (3.3 g) is bubbled into a stirred reaction mixture of the phthalimido enamine obtained in the previous step in anhydrous tetrahydrofuran (210 ml) resulting in the production of a large amount of precipitate. Sodium cyanoborohydride (2.3 g) in dry methanol (50 ml) is added to the stirred suspension over a period of 5 minutes under a stream of $N_2$. When addition is complete, the reaction mixture is stirred at RT for 2½ hours, evaporated in vacuo, and the residue partitioned between ether and 2% KOH solution. The layers are separated and the aqueous layer extracted with additional ether. The combined ether layers are washed with $H_2O$ and then stirred with 5% aqueous HCl solution. The layers are separated and the aqueous acid washed with ether. The acidic layer is made strongly alkaline with 50% sodium hydroxide solution, resulting in the formation of an oily precipitate which is extracted with ether. The ether extract is washed with saturated sodium chloride solution, dried over magnesium sulfate, and evaporated in vacuo, yielding 15.9 g of a clear yellow oil. NMR analysis indicates this oil to be the desired product, which is used without further treatment for the following reaction.

Step 4. 7-(3-Aminopropoxy)-1-dimethylamino-1,2,3,4-tetrahydronaphthalene.

85% hydrazine hydrate solution (3.2 ml) is added to a solution of the phthalimido tetrahydronaphthalene (about 15 g) obtained in the preceding step dissolved in absolute ethanol (160 ml). The stirred reaction mixture is refluxed for 3 hours, after which it is allowed to cool and the resulting precipitate removed by filtration. The clear yellow filtrate is evaporated in vacuo leaving a moist yellow solid, which is triturated in 5% aqueous HCl solution. The resulting thick slurry is filtered and the clear filtrate made strongly alkaline with 50% sodium hydroxide solution, resulting in the formation of an oily precipitate. The precipitate is extracted with diethyl ether and the ether layers washed with saturated sodium chloride solution, dried over sodium sulfate, filtered and the filtrate evaporated in vacuo, yielding 7.8 g of a light amber oil. NMR and IR analysis indicate that this oil is the desired amino product, which is used without further treatment for the next reaction step.

Step 5. 3-Amino-4-[3-[7-(1-dimethylamino-1,2,3,4-tetra hydronaphthyloxy)]propylamino]-1,2,5-thiadiazole-1-oxide.

3,4-Dimethoxy-1,2,5-thiadiazole-1-oxide (4.46 g) is dissolved in methanol (450 ml) and the methanolic solution cooled to 3° C. in an ice bath. 7-(3-aminopropoxy)-1-dimethylamino-1,2,3,4-tetrahydronaphthalene (7.2 g) in 75 ml methanol is slowly added to the stirred mixture and stirring continued at a constant temperature of 3° C. for one hour after addition is complete. Anhydrous ammonia (31 g) is bubbled into the reaction mixture and stirring is continued at RT for 2 hours. The reaction mixture is evaporated in vacuo and the residue triturated in ethyl acetate (75 ml), stirred in ethyl acetate for 1.5 hours, filtered, washed with ethyl acetate and diethyl ether, and dried in vacuo yielding a white powder (8.2 g), M.P. 154°–158° C., comprising more than one compound.

The powder is dissolved in a solution of 10% methanol/methylene chloride, and chromatographed on a silica gel column (250 g; 100–200 mesh) eluting the column with successively more polar solvent combinations of methanol in $CH_2Cl_2$ (10% to 60% methanol). The fractions containing the material with Rf of 0.11 are pooled and evaporated in vacuo, yielding a white solid (3.6 g), which is triturated in ether, filtered and dried, giving 3.2 g of a white powder, M.P. 160°–163° C. (dec). NMR, IR and elemental analysis indicate that this material is the desired thiadiazole-1-oxide product.

EXAMPLE 2

The Preparation of 3-amino-4-[3-[5-(1-dimethylamino-1,2,3,4-tetrahydronaphthloxy)]-propylamino]-1,2,5-thiadiazole-1-oxide Step 1. 5-[3-(N-Phthalimido)propoxy]-1-tetralone.

75.9 g of anhydrous potassium carbonate is added to a stirred solution of 5-hydroxy-1-tetralone (89.1 g) in dimethylformamide (890 ml). The reaction mixture is stirred for 15 minutes, at which time 147 g of N-(3-bromopropyl) phthalimide is added to the reaction mixture. The mixture is stirred at RT overnight. The reaction mixture is extracted with $H_2O$ and methylene chloride. The methylene chloride extracts are washed with $H_2O$, dried over sodium sulfate, filtered, and the filtrate evaporated in vacuo, yielding a dark viscous oil. The oil is dissolved in ethyl acetate, seeded, and allowed to stir at RT for two hours. The resultant solid is filtered, washed with 150 ml ethyl acetate, and allowed to air dry, yielding 72.4 g of a tan solid, M.P. 119°–121° C.

Step 2. 1-Dimethylamino-5-(phthalimido) propoxy-3,4-dihydronaphthalene.

A solution of dimethylamine (40.1 g) in dry toluene (350 ml) is added to a stirred suspension of the tetralone obtained in Step 1 (35 g) suspended in dry toluene (150 ml) under positive $N_2$ pressure. The resultant mixture is cooled in an ice bath to 1° C., followed by the addition of titanium tetrachloride (5.5 ml) in dry toluene (40 ml) over a period of 20 minutes, maintaining a temperature of <0° C. After the addition is complete, the ice bath is removed and the mixture allowed to warm to RT. After stirring for 4½ hours, the mixture is filtered, the salts washed with 400 ml dry toluene and the clear light yellow filtrate evaporated in vacuo, yielding 47 g of a slightly cloudy red-orange oil which is used in the next step without further treatment.

Step 3. 1-Dimethylamino-5-(3-phthalimido) propoxy-1,2,3,4-tetrahydronaphthalene

The dihydronaphthalene of the previous step is dissolved in 350 ml of anhydrous tetrahydrofuran and introduced into a reaction flask under $N_2$. Anhydrous hydrogen chloride (5.9 g) is passed into the stirred solution under $N_2$, followed by the addition of sodium cyanoborohydride (4.0 g) in dry methanol (100 ml) over a period of 10 minutes, resulting in a light yellow cloudy suspension. The suspension is stirred under $N_2$ at RT for about 3 hours. The reaction mixture is evaporated in vacuo at 40°–50° C., and the residue partitioned between 0.1N KOH solution and diethyl ether. The aqueous layer is extracted with ether, and the combined organic extracts washed with $H_2O$ and stirred with 5% aqueous HCl resulting in the formation of a precipitate. The solid is filtered and washed with diethyl ether and 5% HCl. The aqueous filtrate is combined with the solid and the mixture made strongly alkaline. The resultant solution is extracted with diethyl ether. The combined ether extracts are washed with saturated sodium chloride, dried over sodium sulfate, filtered and the filtrate evaporated in vacuo. The resultant viscous amber oil is identified by NMR as the desired product, which is used without further purification for the next step of the reaction sequence.

Step 4. 5-(3-Aminopropoxy)-1-dimethylamino-1,2,3,4-tetrahydronaphthalene.

4.4 ml of 99% hydrazine hydrate are added to a stirred solution of 5-(3-phthalimidopropoxy)-1-dimethylamino-1,2,3,4-tetrahydronaphthalene (26.8 g prepared in the preceding step) in absolute ethanol (270 ml). The reaction mixture is stirred and heated to reflux for 3 hours, allowed to cool, filtered and the filtrate evaporated in vacuo. The yellow residue is triturated in 5% HCl (250 ml), the suspension filtered and the solid washed with 5% HCl. The clear yellow filtrate is extracted with diethyl ether. The aqueous acidic layer is made strongly alkaline with 50% NaOH solution, resulting in an oily precipitate which is extracted with diethyl ether. The combined organic extracts are dried over sodium sulfate, filtered and the filtrate evaporated in vacuo, yielding 14.7 g of a light yellow oil identified by NMR as the desired 3-aminopropoxy compound.

Step 5. 3-Amino-4-[3-[5-(1-dimethylamino-1,2,3,4-tetrahydronaphthyloxy)]]propylamino-1,2,5-thiadiazole-1-oxide.

7.0 g of 5-(3-aminopropoxy)-1-dimethylamino-1,2,3,4-tetrahydronaphthalene, which is obtained in the preceding step, in methanol (70 ml) is added over a period of 1 hour and 10 minutes to a solution of 3,4-dimethoxy-1,2,5-thiadiazole-1-oxide (4.57 g) in methanol (450 ml) and stirred under $N_2$ at a temperature of 2° C. for one hour. Anhydrous ammonia (26 g) is bubbled into the reaction mixture over a period of 10 minutes. The ice bath is removed and the reaction mixture allowed to warm at RT for two hours, after which the resultant mixture is evaporated in vacuo, yielding 11 g of a yellow solid. The yellow solid is suspended in absolute methanol (90 ml) and the suspension heated to boiling for 10 minutes. The cooled suspension is stirred at RT for one hour, filtered, washed with ethanol and ether, and dried at 60° C. (0.25 mm Hg) for two hours. The resultant light yellow powder has a melting point of 198°–199° C. NMR, IR and elemental analysis indicate that the solid is the desired product.

EXAMPLE 3

The Preparation of n-[3-[5-(1-dimethylamino-1,2,3,4-tetrahydronaphthyloxy)]-propyl]-n'-methyl-2-nitro-1,1-diaminoethene 3.58 g of 2-methylamino-2-methylthio-1-nitroethene is added to a solution of 3-[5-(1-dimethylamino-1,2,3,4-tetrahydronaphthyloxy) propylamine (6 g) in absolute ethanol (60 ml). The stirred reaction mixture is refluxed for two hours, while purging the atmosphere above the reaction mixture with $N_2$ to remove evolved methyl mercaptan. The reaction mixture is allowed to cool to RT while stirring for an additional hour. The resultant solid is filtered, washed with ethanol and ether, and dried in a vacuum dessicator at 60°–70° C. for 1½ hours, yielding 4.2 g of a near-white solid, M.P. 160°–164° C. Recrystallization from ethanol results in a white solid, M.P. 161°–165° C. NMR, IR, and elemental analysis indicate that this solid is the desired product.

EXAMPLE 4

The Preparation of 3-amino-4-[3-[5-[1-(1-piperidinyl)]-1,2,3,4-tetrahydronaphthyloxy]]propylamino]-1,2,5-thiadiazole-1-oxide Step 1. 1-(1-Piperidinyl)-5-(3-phthalimido)propoxy-3,4-dihydronaphthalene.

83.8 ml of piperidine are added to a stirred suspension of 5-(3-phthalimido)propoxy-1-tetralone (36.9 g) in dry toluene (370 ml) under $N_2$. The reaction mixture is stirred at RT for several minutes and then cooled in an ice bath to about 1° C. 5.8 ml of titanium tetrachloride in toluene (50 ml) is added to the reaction mixture over a period of 25 minutes, maintaining the temperature at 4°–6° C. The ice bath is removed after the addition is complete. The reaction mixture is stirred for four hours, filtered and the solid washed with dry toluene (300 ml). The filtrate is evaporated in vacuo yielding 47.6 g of a dark red-orange viscous oil. NMR indicates that this oil is the desired dihydronaphthalene product.

Step 2. 1-(1-Piperidinyl)-5-(3-phthalimido)propoxy-1,2,3,4-tetrahydronaphthalene.

The red oil obtained in the previous step is dissolved in anhydrous tetrahydrofuran (350 ml) under an atmosphere of $N_2$. 5.9 g of anhydrous HCl is bubbled into the solution over a period of about two minutes, resulting in a solid precipitate. Maintaining a positive $N_2$ pressure, the suspension is stirred and 4.2 g of sodium cyanoborohydride in dry methanol (100 ml) is added over a period of 10 minutes. After the addition is complete, the reaction mixture is stirred at RT for a period of 3 hours, after which $N_2$ is bubbled vigorously through the mixture for 10 minutes. The mixture is evaporated in vacuo at 40°–45° C. and the residue partitioned between aqueous base and ether. The resulting solids are filtered away and the filtrate layers separated. The aqueous layer is washed with ether and the combined ether extracts washed with $H_2O$ and saturated sodium chloride and dried over sodium sulfate. The combined ether extracts are filtered and the filtrate evaporated in vacuo affording 38.2 g of a slightly cloudy orange oil. NMR indicates that the orange oil is the desired product, which is used without further treatment for the next step of the reaction sequence.

Step 3. 5-(3-Aminopropoxy)-1-(1-piperidinyl)-1,2,3,4-tetrahydronaphthalene.

The orange oil from the preceding step is stirred with absolute ethanol (375 ml) and the ethanol supernatant decanted from the insoluble material. 6.5 ml of an 85% hydrazine hydrate solution is added to the ethanol solution and the reaction mixture refluxed for three hours. The cooled mixture is filtered and the filtrate evaporated in vacuo, yielding a yellow solid foam. The yellow solid is triturated with 5% aqueous HCl, the solids filtered away and the filtrate made strongly alkaline with sodium hydroxide solution. The resulting oily precipitate is extracted with diethyl ether and the organic extract dried over sodium sulfate. The ether solution is filtered and the filtrate evaporated in vacuo affording 21.2 g of an amber oil. Distillation of this oil in vacuo yields two fractions boiling below the range of $\leq 180°$ C. (0.5 mm Hg) to 290° C. (0.5–0.7 mm Hg). These fractions were identified as the desired end product by NMR analysis. (Succinate salt; M.P. =161°–163° C.)

Step 4. 3-Amino-4-[3-[5-[1-(1-piperidinyl)-1,2,3,4-tetrahydronaphthyloxy]]propylamino]-1,2,5-thiadiazole-1-oxide 5-(3-Aminopropoxy)-1-(1-piperidinyl)-1,2,3,4-tetrahydronaphthalene (7.3 g), obtained in the previous step, in methanol (75 ml) is added over a period of 45 minutes to a stirred solution of 3,4-dimethoxy-1,2,5-thiadiazole-1-oxide (4.1 g) in methanol (410 ml) while maintaining a reaction temperature of 2°–3° C. under an atmosphere of $N_2$. After the addition is complete, the solution is stirred in the ice bath for 30 minutes, followed by the addition of 20.7 g of anhydrous ammonia gas bubbled into the reaction mixture over a period of five minutes. The reaction mixture is stirred at RT overnight and the resultant mixture evaporated in vacuo, resulting in 10.7 g of a foamy oil. The oil is dissolved in 10% methanol in methylene chloride (100 ml) and purified on a silica gel column (100-200 mesh; 400 g) using eluents having increasingly greater percentages of methanol. The major fractions are pooled, yielding 3.6 g of a foamy solid. The foamy solid is triturated with boiling absolute ethanol and the cooled solution is filtered. The solid is washed with ethanol and ether and dried at 65°–70° C. at 0.5 mm Hg for two hours, yielding 1.85 g of a white solid having a melting point of 204°–205° C. NMR analysis and elemental analysis identify the white solid as the desired thiadiazole oxide end product.

EXAMPLE 5

Preparation of 3-amino-5-[3-[5-(1-dimethylamino-1,2,3,4-tetrahydronaphthyloxy)]propylamino]-1-methyl-1H-1,2,4-triazole Step 1. 5-(3-N-Phthalimidopropoxy)-1-tetralone Potassium carbonate (94.5 g) is added to a solution of 5-hydroxy-1-tetralone (111 g) dissolved in dimethylformamide (1 liter) and the solution stirred for about 15 minutes. 183.3 g of N-(3-bromopropyl) phthalimide are added to the stirred solution, and the reaction mixture is stirred at RT overnight. The reaction mixture is partitioned between $H_2O$ and methylene chloride, and the aqueous layers extracted with methylene chloride. The combined organic layers are washed with $H_2O$ and dried over sodium sulfate. The organic extract is filtered and the filtrate evaporated in vacuo, yielding a viscous oil which is dissolved in ethyl acetate and stirred at RT for 2 hours. The resultant solid is filtered and dried in air, yielding about 90 g of a yellowish solid, M.P. 118°–121° C. NMR indicates that the solid is the desired phthalimido product.

Step 2. 1-Dimethylamino-5-(3-phthalimidopropoxy)-3,4-dihydronaphthalene.

5-(3-N-Phthalimidopropoxy)-1-tetralone (50 g) is suspended in 120 ml of anhydrous toluene. 57.4 g of dimethylamine in toluene (500 ml) are added to the stirred suspension and the mixture cooled to 1° C. A solution of titanium tetrachloride (7.92 ml) in toluene (60 ml) is added slowly to the stirred suspension, keeping the temperature below 6° C. After the addition is complete, the reaction mixture is allowed to reach RT and stirred for three hours. The reaction mixture is filtered, the filtered salts washed with dry toluene, and the filtrate evaporated in vacuo, yielding 55.7 g of a viscous yellow liquid. NMR indicates that this product is predominently the desired end product, which is used in the following step without any further treatment.

Step 3. 1-Dimethylamino-5-(3-phthalimidopropoxy)-1,2,3,4-tetrahydronaphthalene.

The viscous yellow liquid obtained in the preceding step (55.7 g) is dissolved in anhydrous tetrahydrofuran (450 ml) and anhydrous hydrogen chloride gas (5.9 g) passed through the solution. A gummy precipitate results. The reaction mixture is stirred while 5.6 g of sodium cyanoborohydride in dry methanol (120 ml) is added over a period of ten minutes, resulting in a yellow suspension. The suspension is stirred under $N_2$ at RT for 3 hours and the resultant mixture evaporated in vacuo, yielding 57.4 g of a viscous yellow liquid. The liquid is partitioned between aqueous base and diethyl ether. The aqueous layers are washed with ether and the combined ether layers washed with $H_2O$. The ether extract is stirred with 350 ml of 5% HCl and the resulting precipitate filtered and washed successively with 5% HCl and diethyl ether. The aqueous phases are made strongly alkaline and extracted with ether. The combined ether phases are washed with saturated sodium chloride and dried over sodium sulfate, filtered and evaporated in vacuo, yielding 35 g of crude product, which NMR indicates is primarily the desired tetrahydronaphthalene compound and which is used without further treatment in the next reaction step.

Step 4. 5-(3-Aminopropoxy)-1-dimethylamino-1,2,3,4-tetrahydronaphthalene.

6.7 ml of hydrazine hydrate is added to a solution of the crude product obtained in the previous reaction step dissolved in ethanol (400 ml). The reaction mixture is stirred under reflux for 3 hours and allowed to stir at RT overnight. The reaction mixture is filtered, the filtered solid washed with ethanol, and the filtrate evaporated in vacuo, affording a yellow solid. The solid is treated with 5% HCl (250 ml), the resulting suspension filtered, and the filtrate extracted with diethyl ether. The aqueous portion is made basic, resulting in the formation of a yellow oil. The aqueous portion is extracted with diethyl ether and the combined ether extracts dried over sodium sulfate, filtered and evaporated in vacuo, yielding 17 g of a viscous yellow liquid. NMR analysis indicates that the crude product is the desired aminopropoxy tetrahydronaphthalene.

Step 5. 1-Cyano-3-[3-[5-(1-dimethylamino-1,2,3,4-tetrahydronaphthyloxy)]propyl]-2-methylpseudothiourea.

9.9 g of the amine obtained in the previous step in isopropyl alcohol (25 ml) are added over a period of ten minutes to a solution of S,S-dimethyl-N-cyanoiminodithiocarbonimidate (6.5 g) in isopropanol (100 ml). The reaction mixture is stirred at RT overnight and evaporated in vacuo, yielding a green oil. TLC and IR spectra indicate that this oil is the desired product, which is used in the next step without further treatment.

Step 6. 3-Amino-5-[3-[5-(1-dimethylamino-1,2,3,4-tetrahydronaphthyloxy)]propylamino]-1-methyl-1H-1,2,4-triazole.

4.5 g of methyl hydrazine is added to a stirred solution of the cyanopseudothiourea obtained in the preceding step (about 6 g) in dimethylformamide (60 ml). The reaction mixture is stirred for about 20 hours at a temperature of 40° C., after which it is evaporated in vacuo, yielding 13 g of a brown oil. The oil is triturated in anhydrous ether, filtered and dried, yielding 4.9 g of a green powder consisting of 2 major products. The green powder is dissolved in 10% methanol and methylene chloride and run through a silica gel column (200 g) eluting the column with successively more polar combinations of methanol and methylene chloride. The major product fractions are pooled and evaporated in vacuo, resulting in 2.6 g of a light brown solid, which is triturated in boiling acetonitrile, cooled and filtered. The solid is washed with acetonitrile and diethyl ether and dried at elevated temperature in vacuo, resulting in the desired triazole product as a near-white powder, M.P. 171°-173° C.

EXAMPLE 6

The Preparation of 2-cyano-1-[3-[5-(1-dimethylamino-1,2,3,4-tetrahydronaphthyloxy)]propyl]-3-methyl guanidine 10.5 g of anhydrous methylamine in absolute ethanol (75 ml) is combined with a solution of 1-cyano-3-[3-[5-(1-dimethylamino-1,2,3,4-tetrahydronaphthyloxy)]-propyl]-2-methylpseudothiourea (about 6 g) in absolute ethanol (100 ml). The reaction mixture is stirred at RT overnight while purging with $N_2$ to remove the methyl mercaptan. The reaction mixture is evaporated in vacuo, yielding 8.0 g of a dark oil, which is separated on a silica gel column (375 g), eluted with methanol in methylene chloride at increasingly greater concentrations of methanol (10% to 40%). The major pure fractions are pooled together and evaporated in vacuo, resulting in 4.1 g of a brown glass. The glass is dissolved in 50 ml of methanol and 2.1 g of O-benzoic sulfimide added to the solution. The resulting solution is evaporated in vacuo, yielding a dark oil which is triturated in anhydrous ether, the resultant solid filtered, washed with ether and allowed to air dry. The resulting solid has a melting point of 160°-165° C. The solid is dissolved in hot methanol, filtered while hot, allowed to cool, and the resultant solution diluted with an equal volume of anhydrous ether. The resultant solid is filtered, washed with methanol/diethyl ether (1:1), diethyl ether and air dried, yielding 3.5 g of a light gray solid, M.P. 171°-173° C., with shrinkage beginning at 169° C. NMR, IR and elemental analysis indicate that this solid is the desired 2-cyano guanidine saccharinate.

EXAMPLE 7

The Preparation of 3-amino-5-[3-[5-[1-(1-piperidinyl)-1,2,3,4-tetrahydronaphthloxy]]propylamino]-1-Methyl-1H-1,2,4-triazole Step 1. 1-Cyano-2-methyl-3-[3-[5-[1-(1-piperidinyl)-1,2,3,4-tetrahydronaphthyloxy]]propyl]pseudothiourea.

2.9 g of 5-(3-aminopropoxy)-1-(1-piperidinyl)-1,2,3,4-tetrahydronaphthylene in isopropanol (15 ml) are added over a period of 3 minutes to a stirred solution of S,S-dimethyl-N-cyanoiminodithiocarbonimidate (1.6 g) dissolved in isopropanol (20 ml). The reaction mixture is stirred at RT overnight, resulting in the formation of a solid precipitate. The solid is filtered, washed with isopropanol and diethyl ether, and dried in air and at 0.75 mm Hg, resulting in 2.9 g of a white powder, M.P. 141°-144° C. NMR and elemental analysis indicate the white powder is the desired product.

Step 2. 3-Amino-5-[3-[5-[1-(1-piperidinyl)-1,2,3,4-tetrahydronaphthyloxy]]propylamino]-1-methyl-1H-1,2,4-triazole.

Methyl hydrazine (2 ml) is added to a stirred suspension of the pseudothiourea obtained in the previous step (2.40 g) suspended in dimethylformamide (20 ml). The reaction mixture is heated and stirred at a temperature between 40°-45° C. for 24 hours. The reaction mixture is allowed to cool and evaporated in vacuo. The moist residue is triturated with anhydrous diethyl ether, the resultant solid filtered, washed with ether and allowed to air dry, yielding a white powder which is twice recrystallized from ethyl acetate and dried, M.P. 165.5°-167° C. NMR, IR and elemental analysis indicate that this product is the desired triazole.

EXAMPLE 8

The Preparation of n-[3-[7-(1-dimethylamino-1,2,3,4-tetrahydronaphthyloxy) propyl]-N'-methyl-2-nitro-1,1-diaminoethene Step 1. 1-Dimethylamino-7-methoxy-3,4-dihydronaphthalene.

A solution of titanium tetrachloride (53.8 g, 31.2 ml) in dry toluene (200 ml) is added over a period of 45 minutes to a stirred solution of 7-methoxy-1tetralone (100.5 g) and dimethyl amine (171 g) in dry toluene (2 l) while maintaining a reaction temperature of ≦10° C. When the addition of the titanium is complete, the ice bath is removed and the solution allowed to reach RT. The solution is stirred at RT for 3 hours. The solids are filtered, washed with dry toluene and the filtrate evaporated in vacuo, yielding 101.4 g of an amber oil which is used in the next step without further treatment.

Step 2. 7-Methoxy-1-dimethylamino-1,2,3,4-tetrahydronaphthalene.

A solution of 95% sodium cyanoborohydride (22.5 g) in methanol (500 ml) is added slowly to a stirred solution of the methoxy dihydronaphthalene of the previous step in tetrahydrofuran (1.6 l) to which has previously been added anhydrous hydrochloric acid (23.4 g). The addition is accomplished under an atmosphere of $N_2$. The reaction mixture is stirred at RT for 3 hours, $N_2$ vigorously bubbled through the reaction mixture and the mixture evaporated in vacuo, yielding a cloudy oil. The oil is taken up in 2% KOH (1 liter) and partitioned between base and diether ether. KOH pellets are added until the aqueous layer is made basic, the layers separated, and the aqueous layer washed with ether. The combined ether extracts are washed with $H_2O$ and stirred with 5% HCl for 15 minutes. The acidic layer is washed with ether and then made basic with 50% sodium hydroxide solution. The resultant aqueous layer is extracted with ether, the ether extract dried over sodium sulfate, filtered and evaporated in vacuo, yielding about 90 g of a gold oil identified by NMR and IR as the desired tetrahydronaphthalene product.

Step 3. 7-Hydroxy-1-dimethylamino-1,2,3,4-tetrahydronaphthalene.

90 g of 7-methoxytetrahydronaphthalene obtained in the previous step are dissolved in glacial acetic acid (1 liter). 48% hydrobromic acid (1 liter) is added to the solution and the resulting reaction mixture heated to reflux for 3 hours. The reaction mixture is poured into 4 liters of $H_2O$ and crushed ice and the solution made alkaline to pH 8 to 9. The aqueous mixture is extracted with methylene chloride. The methylene chloride extract is back-extracted with 2% KOH solution and the combined basic layers made acidic by the addition of aqueous HCl. The addition is continued until a white precipitate appears at pH about 8-9. The aqueous solution is extracted with methylene chloride and the organic layer washed with $H_2O$, dried, filtered and evaporated in vacuo, yielding a brown oil identified by NMR to be the desired phenol.

Step 4. 1-Dimethylamino-7-[3-(N-phthalimido) propoxy]-1,2,3,4-tetrahydronaphthalene.

Potassium t-butoxide (3.0 g) is added to a stirred solution of 1-dimethylamino-7-hydroxy-1,2,3,4-tetrahydronaphthalene (5.2 g) in dimethylformamide (50 ml). 13.2 g of N-(3-bromopropyl) phthalimide is added to the stirred reaction mixture and stirring continued for about 24 hours. The reaction is partitioned between slightly basic $H_2O$ and diethyl ether. The layers are separated and the aqueous layer extracted with ether. The combined ether extracts are washed with 5% sodium hydroxide solution and $H_2O$. The ether extract is stirred with 5% aqueous hydrochloric acid solution, the layers separated and the ether extracted with additional aqueous 5% hydrochloric acid. The combined acidic aqueous layers are washed with ether and made strongly alkaline, resulting in an oily precipitate. The precipitate is extracted with diethyl ether which is washed with $H_2O$ and saturated sodium chloride solution dried and evaporated in vacuo, yielding 4.4 g of a light yellow glassy solid. NMR analysis indicates that the solid is the desired tetrahydronaphthalene product.

Step 5. 7-(3-Aminopropoxy)-1-dimethylamino-1,2,3,4-tetrahydronaphthalene.

85% hydrazine hydrate (9.6 ml) is added to a stirred solution of the phthalimido tetrathydronaphthalene prepared as described in the previous step (about 50 g) in absolute ethanol (about 500 ml). The reaction mixture is heated at reflux for about 3 hours and allowed to cool. The resulting precipitate is removed by filtration and washed with absolute ethanol. The filtrate is evaporated in vacuo and the residue triturated with 5% aqueous hydrochloric acid. The aqueous suspension is filtered and the solid washed with 5% hydrochloric acid. The filtrate is made strongly alkaline with 50% sodium hydroxide solution, resulting in an oily precipitate which is extracted into diethyl ether. The ether extract is washed with saturated sodium chloride solution, dried, filtered and the filtrate evaporated in vacuo, yielding 28.5 g of the desired amine as an amber oil. NMR, IR and elemental analysis verify the amine structure.

Step 6. N-[3-[7-(1-Dimethylamino-1,2,3,4-tetrahydronaphthyloxy) propyl]-N'-methyl-2-nitro-1,1-diaminoethene.

1-Methylamino-1-methylthio-2-nitroethene (3.58 g) is added to a solution of the tetrahydronaphthyloxy amine prepared in the preceding step (6.0 g) in absolute ethanol (60 ml). The reaction mixture is heated to reflux for about 2 hours while purging the reaction mixture with $N_2$. The mixture is allowed to cool and the resultant solid filtered, washed with diethyl ether and dried, yielding about 2.9 g of a white solid. The filtrate is evaporated in vacuo and the residue dissolved in hot absolute ethanol. Diethyl ether is added, resulting in the formation of a solid which is filtered and dried, giving 1.4 g of a white solid, M.P. 148°-152° C. The two solids are combined and dissolved in boiling isopropyl alcohol, allowed to cool, filtered, washed with isopropyl alcohol and ether, and dried under vacuum. The resulting white powder (2.7 g) has a melting point of 153°-157° C. NMR and elemental analysis identify the solid as the desired diaminoethene product.

EXAMPLE 9

The Preparation of 3-amino-5-[3-[7-(1-dimethylamino-1,2,3,4-tetrahydronaphthyloxy)]propylamino]-1-methyl-1H-1,2,4-triazole Step 1. 7-(3-N-Phthalimidopropoxy)-1-tetralone.

Sodium methoxide (19.8 g) is added to a cooled, stirred solution of 7-hydroxy-1-tetralone (59.5 g) dissolved in dimethylformamide (600 ml). After addition is complete and reaction mixture is stirred for 3 minutes, N-(3-bromopropyl) phthalimide (98.3 g) is added and the reaction mixture stirred overnight. The reaction mixture is poured into $H_2O$ and stirred for an hour, filtered, the solid washed with $H_2O$ and dried in air to give 134 g of a brown solid. The brown solid is recrystallized from hot ethyl acetate, yielding 43.5 g of a white fluffy solid, M.P. 148°-150° C. NMR identifies the recrystallized product as the desired phthalimide.

Step 2. 1-Dimethylamino-7-(3-N-phthalimidopropoxy)-3,4-dihydronaphthalene.

7-(3-N-Phthalimidopropoxy)-1-tetralone (93.5 g) is suspended in a solution of dimethyl amine (101.3 g) in toluene (1 liter) under $N_2$. The stirred suspension is cooled to about 1° C. and titanium tetrachloride (14.6 ml, 25.2 g) in toluene (100 ml) is added to the stirred suspension over a period of 45 minutes, keeping the temperature below 7° C. After addition is complete, the reaction mixture is allowed to reach RT and stirred for 4½ hours. The reaction mixture is filtered and the filtered solid washed with dry toluene. The toluene filtrate is evaporated in vacuo, yielding about 100 g of a yellow oily liquid, identified by NMR as the desired product.

Step 3. 1-Dimethylamino-7-(3-N-phthalimidopropoxy)-1,2,3,4-tetrahydronaphthalene.

Sodium cyanoborohydride (10.2 g) in dry methanol (150 ml) is added slowly with stirring to a solution of the phthalimido dihydronaphthalene prepared in the preceding step (about 100 g) in anhydrous tetrahydrofuran (550 ml) in which 16 g of anhydrous hydrogen chloride is dissolved. At the end of the addition, the reaction mixture comprises a fine suspension and is stirred at RT for 3 hours under $N_2$. The reaction mixture is evaporated in vacuo, resulting in a viscous liquid which is partitioned between 5% potassium hydroxide solution and diethyl ether. The layers are separated and the basic layer washed with ether. The ether extracts are combined and stirred with 5% HCl. The aqueous layer is washed with ether and then made strongly basic with 50% sodium hydroxide solution. The basic aqueous extract is washed with ether and the ether extract washed with sodium chloride, dried, filtered and the ether solution evaporated in vacuo to yield a pale yellow solid. NMR indicates that this solid is the desired tetrahydronaphthalene product.

Step 4. 1-Dimethylamino-7-(3-aminopropoxy)-1,2,3,4-tetrahydronaphthalene.

Hydrazine hydrate (3.56 g) is added to a solution of the tetrahydronaphthalene obtained in the preceding step dissolved in 180 ml of absolute ethanol. The reaction mixture is stirred and heated to reflux for 3 hours. The resultant solid is filtered and the filtrate evaporated in vacuo, yielding a pale yellow solid. The solid is triturated with 5% HCl, the resultant thick slurry filtered, and the solid washed with 5% HCl. The acidic phase is made strongly basic with sodium hydroxide solution until a gold oil appears. The solution is extracted with ether, the ether washed with saturated sodium chloride solution and dried over sodium sulfate. The sodium sulfate is filtered and the ether evaporated in vacuo, resulting in the desired amine product as a viscous oil.

Step 5. 1-Cyano-3-[3-[7-(1-dimethylamino-1,2,3,4-tetrahydronaphthyloxy)]propyl]-2-methylpseudothiourea.

The amine obtained in the preceding step (8.6 g) dissolved in isopropanol (35 ml) is added over a period of one minute to a stirred solution of S,S-dimethyl-N-cyanoiminodithiocarbonimidate (5.6 g) dissolved in 70 ml of isopropanol. The reaction mixture is stirred at RT overnight and then evaporated in vacuo, yielding 13.6 g of the desired cyano product as a viscous amber oil.

Step 6. 3-Amino-5-[3-[7-(1-dimethylamino-1,2,3,4-tetrahydronaphthyloxy)]propylamino]-1-methyl-1H-1,2,4-triazole.

Methyl hydrazine (11 ml) is added to a stirred solution of the cyanotetrahydronaphthalene obtained in the previous step (about 10 g) dissolved in dimethylformamide (110 ml). The reaction mixture is stirred at about 40° C. for 24 hours, and evaporated under vacuum resulting in a residue of amber oil (16.2 g). The oil is separated on a silica gel column (290 g; 70–230 mesh) using as eluent methanol in methylene chloride ranging from 10% methanol to 30% methanol. The major fractions are pooled and evaporated in vacuo, resulting in 6.7 g of a viscous amber oil. The oil is triturated in anhydrous ether, resulting in the formation of a solid which is filtered, washed with ether and dried, resulting in 5.4 g of a near-white solid, M.P. 120°–125° C. This solid is recrystallized from hot acetonitrile and dried under vacuum, resulting in 3.5 g of a near-white powder, M.P. 127°–130° C. NMR, IR and elemental analysis indicate the solid as the desired triazole product.

EXAMPLE 10

The Preparation of 3-amino-4-]3-[6-(1-dimethylamino-1,2,3,4-tetrahydronaphthyloxy)]propylamino]-1,2,5-thiadiazole-1-oxide Step 1. 6-(3-N-Phthalimidopropoxy)-1-tetralone.

77.5 g of N-bromopropylphthalimide are added to a stirred solution of 6-hydroxy-1-tetralone (48.6 g) and potassium carbonate (39.9 g) in dimethylformamide (480 ml). The reaction mixture is stirred at RT overnight, and then poured into a stirred mixture of $H_2O$ and methylene chloride. The layers are separated and the aqueous portion washed with methylene chloride. The combined methylene chloride fractions are washed with $H_2O$, dried over sodium sulfate, filtered and the filtrate evaporated in vacuo, yielding an off-white solid which is recrystallized from absolute ethanol, yielding 73.1 g of crystals, M.P. 143°–145° C.

Step 2. 1-Dimethylamino-6-(3-N-phthalimidopropoxy)-3,4-dihydronaphthalene.

Dimethylamine (81.6 g) in dry toluene (600 ml) is added to a stirred suspension of 6-(3-N-phthalimidopropoxy)-1-tetralone (71.3 g) in dry toluene (200 ml) kept at a temperature of 0° C. under $N_2$. Titanium tetrachloride (19.3 g, 11.2 ml) in dry toluene (80 ml) is added slowly to the stirred suspension, keeping the temperature of the reaction mixture below 10° C. The reaction mixture is stirred under $N_2$ overnight, after which it is filtered, the salts washed with dry toluene and the filtrate evaporated in vacuo, yielding 85.9 g of a yellow viscous liquid used as is in the next step without further purification.

Step 3. 1-Dimethylamino-6-(3-N-phthalimidopropoxy)-1,2,3,4-tetrahydronaphthalene.

Sodium cyanoborohydride (9.26 g of 95%) in dry methanol (220 ml) is added slowly to a vigorously stirred mixture of the dihydronaphthalene obtained in the previous step (85.9 g) dissolved in tetrahydrofuran (600 ml) in which anhydrous hydrogen chloride (15 g) has been dissolved. The reaction mixture is stirred at RT overnight under $N_2$. Another 200 ml of methanol is added to the reaction mixture and nitrogen gas bubbled through the mixture for 10 minutes. The resulting solution is evaporated in vacuo, yielding a brown oil which is partitioned between aqueous base and diethyl ether. The aqueous layer is washed with ether and the combined ether portions washed with $H_2O$ and stirred with aqueous 5% HCl. The resultant precipitate is filtered and combined with the separated aqueous layer. The aqueous layer is made alkaline and extracted with ether, and the combined ether portions are washed with saturated sodium chloride and $H_2O$, dried over sodium sulfate and filtered. The filtrate is evaporated, resulting in 52 g of a viscous yellow liquid. NMR analysis indicates that the yellow liquid is the desired tetrahydronaphthalene.

Step 4. 1-Dimethylamino-(3-aminopropoxy)-1,2,3,4-tetrahydronaphthalene.

80% hydrazine hydrate (10.0 ml) is added to a stirred solution of the phthalimido tetrahydronaphthalene obtained in the previous step (52 g) dissolved in absolute ethanol (500 ml). The reaction mixture is refluxed for 3 hours, allowed to cool, and the resultant solid filtered and the filtrate evaporated in vacuo. The yellow solid residue is triturated with aqueous 5% HCl, filtered, washed with aqueous HCl, and the filtrate extracted with ether. The acidic aqueous portion is made basic with 50% sodium hydroxide. The resultant diphasic mixture is extracted with ether, the ether extracts dried, filtered, and evaporated, yielding a yellow viscous liquid (30.1 g). The liquid is dried under high vacuum, yielding 27.7 g of the crude product, which is used as is in the next step.

Step 5. 3-Amino-4-[3-[6-(1-dimethylamino-1,2,3,4-tetrahydronaphthyloxy)]propylamino]-1,2,5-thiadiazole-1-oxide 1-Dimethylamino-(3-aminopropoxy)-1,2,3,4-tetrahydronaphthalene (7.0 g) in methanol (70 ml) is added over a period of 1 hour to a stirred solution of 3,4-dimethoxy-1,2,5-thiadiazole-1-oxide (4.57 g) in methanol (450 ml) cooled to a temperature of 2° C. under $N_2$. Anhydrous ammonia (30 g) is bubbled over a period of 10 minutes into the reaction mixture and the solution stirred at RT overnight. The reaction mixture is evaporated in vacuo, yielding a yellow solid (10.4 g). The solid is dissolved in 10% methanol and methylene chloride mixed with Celite and filtered. The cloudy filtrate is evaporated in vacuo, yielding a glass which is chromatographed on a column of silica gel (350 g) eluting the column with methanol in methylene chloride ranging from a methanol percentage of 10% to 60% methanol. The fractions having an Rf of 0.07 are pooled and evaporated in vacuo, yielding 3.5 g of a dark oil. The oil is triturated in ether, the solid filtered, washed with ether and dried in high vacuum, giving 2.76 g of a near-white powder, M.P. 149°–152° C. The powder is dissolved in hot absolute ethanol and ether, the gummy precipitate filtered, and the filtrate evaporated in vacuo, triturated in ether, filtered, and the solid dried under high vacuum, giving 2.1 g of a near-white powder, M.P. 157°–159° C. (dec). NMR, IR and elemental analysis indicate the desired product.

EXAMPLE 11

Preparation of 3amino-4-[3-[5-[[1-(n-morpholinyl)]-1,2,3,4-tetrahydronaphthyloxyp]]propylamino]-1,2,5-thiadiazole-1-oxide Step 1. 5-Methoxy-(1-(N-morpholinyl))-3,4-dihydronaphthalene.

Titanium tetrachloride (15.2 g) in dry toluene (105 ml) is added slowly to a stirred solution of 5-methoxy-1-tetralone (49 g), and morpholine (160 g) in dry toluene (1 l) cooled in an ice bath to a temperature of 3° C. under a nitrogen atmosphere. The reaction mixture is allowed to warm to RT and stirred at RT under $N_2$ overnight. The reaction mixture is filtered, the filtered solid washed with dry toluene and dry THF and the combined filtrates evaporated in vacuo to a yellow solid (63.5 g), M.P. 80°–90° C.

Step 2. 5-Methoxy-1-(N-morpholinyl)-1,2,3,4-tetrahydronaphthalene.

95% sodium cyanoborohydride (10.2 g) in methanol (225 ml) is added to a stirred reaction mixture of the 5-methoxy dihydronaphthalene obtained in the previous step (about 63 g) and 11.7 g of anhydrous hydrochloric acid dissolved in anhydrous tetrahydrofuran (1 liter). The reaction mixture is stirred at RT for 3 hours, $N_2$ gas vigorously bubbled through the reaction mixture and the resulting suspension evaporated in vacuo, yielding a whitish solid. The solid residue is partitioned between aqueous base and methylene chloride, the alkaline layer washed with methylene chloride and the combined methylene chloride portions washed with $H_2O$. The methylene chloride extract is stirred with aqueous 5% HCl, the layers separated and the organic layer again washed with aqueous 5% HCl. The aqueous layer is made extremely basic with 50% sodium hydroxide solution and the basic solution extracted with methylene chloride. The methylene chloride extract is washed with $H_2O$, dried, filtered, and the filtrate evaporated in vacuo, yielding 18.3 g of an oil which later solidifies. NMR analysis indicates that the crude product is the desired compound, which is used without further treatment in the next synthetic step.

Step 3. 5-Hydroxy-1-morpholinyl-1,2,3,4-tetrahydronaphthalene.

48% hydrobromic acid (180 ml) is added to a stirred solution of the crude tetrahydronaphthalene obtained in the previous step (18.3 g) dissolved in glacial acetic acid (180 ml) under an atmosphere of $N_2$. The reaction mixture is refluxed under $N_2$ for 3 hours, after which it is poured into crushed ice, resulting in the formation of a green precipitate. The precipitate is filtered and the filtrate extracted with ether. The aqueous layer is made basic (pH 8-9) forming a white precipitate. The precipitate is extracted with ether, the layers separated, and the ether portion washed with $H_2O$, dried over sodium sulfate, filtered and evaporated in vacuo, resulting in a white crystalline solid (14.9 g), M.P. 194°–196° C. NMR indicates the desired phenolic product.

Step 4. 5-(3-Phthalimidopropoxy)-1-(N-morpholinyl)-1,2,3,4-tetrahydronaphthalene.

Potassium t-butoxide (7.8 g) is added to a stirred solution of 5-hydroxy-1-morpholinyl-1,2,3,4-tetrahydronaphthalene (14.7 g) dissolved in dimethylformamide (150 ml) and the reaction solution stirred for a few minutes. N-(3-bromopropyl) phthalimide (33.8 g) is added to the reaction mixture and stirring is continued at RT for 2 days. The reaction mixture is partitioned between $H_2O$ and ether, the layers separated and the aqueous layer adjusted to a pH>10 with sodium hydroxide solution and extracted with additional diethyl ether. The combined ether layers are washed with $H_2O$ and aqueous 5% hydrochloric acid. The acidic aqueous extracts are made strongly alkaline with sodium hydroxide solution, resulting in an oily precipitate which is extracted with ether and methylene chloride. The combined organic layers are washed with 5% aqueous sodium hydroxide and saturated sodium chloride, dried over sodium sulfate, filtered, and evaporated, resulting in 22.6 g of an amber oil as the crude product used in the next step.

Step 5. 5-(3-Aminopropoxy)-1-(N-morpholinyl)-1,2,3,4-tetrahydronaphthalene.

85% hydrazine hydrate (3.3 ml) is added to a suspension of the phthalimido tetrahydronaphthalene obtained in the preceding step (21.9 g) in absolute ethanol (200 ml). The reaction mixture is heated to reflux with stirring for 3½ hours, after which the reaction mixture is allowed to cool, filtered and the solid washed with ethanol. The ethanol filtrate is evaporated in vacuo, yielding 3.4 g of a solid. The solid and residue are combined and stirred with 5% aqueous HCl, the mixture filtered and the solid washed with 5% HCl. The filtrate is made strongly alkaline with 50% sodium hydroxide solution, resulting in the formation of an oily precipitate which is extracted with methylene chloride. The methylene chloride extract is washed with saturated sodium chloride solution, dried over sodium sulfate, filtered and evaporated in vacuo, yielding 13.2 g of an amber oil which is identified by NMR analysis to be the desired amine product.

Step 6. 3-Amino-4-[3-[5-[1-(N-morpholinyl)-1,2,3,4-tetrahydronaphthyloxy]]propylamino]-1,2,5-thiadiazole-1-oxide 5-(3-Aminopropoxy)-1-(N-morpholinyl)-1,2,3,4-tetrahydronaphthalene (6.3 g) in methanol (60 ml) is added over a period of one hour to a stirred solution of 3,4-dimethoxy-1,2,5-thiadiazole-1-oxide (3.35 g) in methanol (350 ml), cooled in an ice bath under an atmosphere of $N_2$. The reaction mixture is stirred in an ice bath for 2½ hours, followed by the addition of anhydrous ammonia (25.0 g) bubbled into the reaction mixture over a period of 10 minutes. The solution is stirred at RT for 2 hours, after which the reaction mixture is evaporated in vacuo, resulting in 9.3 g of a solid. The solid is ground into a powder and suspended in absolute ethanol. The suspension heated to boiling, cooled, and the cooled suspension filtered. The solid is washed with ethanol and ether, and dried under vacuum, giving 4.8 g of a white solid, M.P. 198°–200° C. (dec). NMR and elemental analysis establish this solid as the desired triazole product.

EXAMPLE 12

PREPARATION OF 3-AMINO-5-[3-[5-[[1-(N-MORPHOLINYL)]-1,2,3,4-TETRAHYDRONAPHTHYLOXY]] PROPYLAMINO]-1-METHYL-1H-1,2,4-TRIAZOLE

A mixture of 5-(3-aminopropoxy)-1-(N-morpholinyl)-1,2,3,4-tetrahydronaphthalene (5.2 g) and the methyl ester of N-cyano-1-methyl-2-(phenylmethylene)hydrazinecarboxyimidothioic acid (4.0 g) is heated neat to a temperature of 70° C. in a vacuum of 15 mm Hg for a period of 4½ hours. The resultant neat mixture is cooled and triturated in acetone, resulting in a solid precipitate. The addition of 5% aqueous hydrochloric acid affords a clear light-green solution which is stirred at RT for an hour, diluted with $H_2O$ and washed with diethyl ether. The aqueous solution is made strongly alkaline with 50% sodium hydroxide solution resulting in an oily precipitate, which is extracted with ethyl acetate. The ethyl acetate extract is washed with saturated sodium chloride, dried over sodium sulfate, filtered and the filtrate evaporated in vacuo, resulting in 6.9 g of a viscous amber oil. The oil is dissolved in hot acetonitrile, filtered, the acetonitrile solution allowed to cool, and the resultant precipitate filtered, yielding 3.38 g of a solid, M.P. 150°–153° C. NMR, IR and elemental analysis indicate the solid to be the desired triazole product.

EXAMPLE 13

PREPARATION OF 3-AMINO-4-[3-[5-(1-PYRROLIDINYL-1,2,3,4-TETRAHYDRONAPHTHYLOXY)] PROPYLAMINO]-1,2,5-THIADIAZOLE-1-OXIDE

Step 1. 5-Methoxy-1-pyrrolidinyl-3,4-dihydronaphthalene.

Titanium tetrachloride (31.1 ml) in dry toluene (210 ml) is added slowly to a stirred solution of 5-methoxy-1-tetralone (100 g) and pyrrolidine (263 g) in anhydrous toluene (2 l) cooled in a methanol ice bath under $N_2$ while maintaining a temperature of less than 7° C. When the addition is complete, the reaction mixture is allowed to stir at RT for 3½ hrs. The reaction mixture is filtered, the solid washed with anhydrous toluene, and the filtrate evaporated in vacuo, resulting in a gold viscous liquid, which is dissolved in 1.8 l of dry tetrahydrofuran and filtered. The filtrate is used as is in the next step.

Step 2. 5-Methoxy-1-pyrrolidinyl-1,2,3,4-tetrahydronaphthalene.

Anhydrous hydrochloric acid in methanol (23 g) is added to the filtrate obtained in the previous step, while stirring the mixture under $N_2$. Sodium cyanoborohydride (22.7 g) in methanol (180 ml) is added slowly to the reaction mixture with vigorous stirring. The resultant suspension is stirred under $N_2$ for almost 3 hrs at RT, nitrogen gas is bubbled through the solution and the solution evaporated in vacuo. The resultant viscous liquid is taken up in aqueous base and diethyl ether. The aqueous layer is made strongly basic with solid potassium hydroxide and the layers separated. The aqueous layer is washed with ether and the ether portions combined and stirred with 5% aqueous hydrochloric acid solution. The ether portion is separated and washed with additional hydrochloric acid solution. The combined aqueous portions are made alkaline, resulting in the formation of an immiscible liquid which is extracted with ether. The ether extract is washed with $H_2O$, dried and evaporated in vacuo, resulting in a solid identified as the desired material. The solid is used in the next step without purification.

Step 3. 5-Hydroxy-1-pyrrolidinyl-1,2,3,4-tetrahydronaphthalene.

48% hydrobromic acid (1 l) is added to a stirred solution of the methoxy tetrahydronaphthalene obtained in the previous step dissolved in glacial acetic acid (1 l) under an atmosphere of nitrogen. The reaction mixture is heated to reflux for 2 hrs, then poured into $H_2O$/crushed ice and sodium hydroxide pellets added until a white solid appears. Aqueous base is used to adjust the pH to about 8 to 9. The mixture is filtered, and the filtered solid is ground and suspended in $H_2O$ and filtered again. The solid is recrystallized from ethyl acetate, yielding a whitish solid, M.P. 151°–153° C. NMR analysis indicates that the product is the desired 5-hydroxy-tetrahydronaphthalene.

Step 4. 5-(3-N-Phthalimidopropoxy)-1-N-pyrrolidinyl-1,2,3,4-tetrahydronaphthalene.

Potassium t-butoxide (30.9 g) is added to a solution of 5-hydroxy-1-(N-pyrrolidinyl)-1,2,3,4-tetrahydronaphthalene (65.3 g) in dimethylformamide (650 ml). The reaction mixture is stirred for 5 minutes, after which N-(3-bromopropyl) phthalimide (134.5 g) is added to the reaction mixture. Stirring is continued over the weekend. The reaction mixture is diluted with $H_2O$ and extracted with ether. The aqueous portion is made basic with 50% sodium hydroxide solution and again extracted with ether. The combined ether extracts are washed with $H_2O$, stirred with 5% sodium hydroxide solution, the basic layers back-extracted with ether and the combined ether extracts washed with $H_2O$ and stirred with 5% aqueous hydrochloric acid solution. The layers are separated and the ether washed with 5% aqueous hydrochloric acid solution and the combined aqueous acid extracts made alkaline with 50% sodium hydroxide solution, resulting in a white precipitate. The precipitate is extracted with ether and methylene chloride and the aqueous portion extracted with methylene chloride. The combined organic extracts are dried, filtered and evaporated in vacuo, resulting in 67.1 g of a pinkish solid. The solid is recrystallized from ethanol, filtered, dried in vacuo, yielding about 51 g of dry product, which is used without further purification in the next step.

Step 5. 5-(3-Aminopropoxy)-1-(N-pyrrolidinyl)-1,2,3,4-tetrahydronaphthalene.

85% hydrazine hydrate (8.3 ml) is added to a stirred solution of the phthalimido pyrrolidinyl tetrahydronaphthalene obtained in the previous step (about 51 g) dissolved in absolute ethanol (500 ml), and the reaction mixture is heated to reflux for 3 hours and then allowed to cool. A precipitate forms upon cooling, and the reaction mixture is filtered, the precipitate washed with absolute ethanol, and the filtrate evaporated in vacuo, resulting in a solid. The solid is triturated with 5% aqueous HCl, filtered, and the solid washed with additional 5% HCl solution. The acidic filtrate is washed with diethyl ether and made basic with 50% aqueous sodium hydroxide, resulting in the formation of a golden oil. The oil is extracted with diethyl ether, washed with $H_2O$, dried over sodium sulfate, filtered and evaporated in vacuo, resulting in 17 g of a golden oil. NMR analysis indicates that this oil is the desired amino product.

Step 6. 3-Amino-4-[3-[5-(1-pyrrolidinyl-1,2,3,4-tetrahydronaphthyloxy)]propylamino]-1,2,5-thiadiazole-1-oxide.

5-(3-Aminopropoxy)-1-(N-pyrrolidinyl)-1,2,3,4-tetrahydronaphthalene (7.0 g) in methanol (100 ml) is added over a period of 90 minutes to a stirred solution of 3,4-dimethoxy-1,2,5-thiadiazole-1-oxide (4.14 g) in methanol (450 ml), while maintaining the temperature at less than 3° C. The reaction mixture is stirred for an additional 1½ hours, after which anhydrous ammonia is bubbled into the reaction mixture over a period of 10 minutes. The reaction mixture is stirred at ambient temperature overnight, evaporated in vacuo, yielding 9.9 g of an off-white solid. The solid is triturated with ethyl acetate, filtered, and the solid dissolved in 10% methanol in methylene chloride. The methanolic solution is placed on a silica gel column (silica gel: Kiesel gel 60, 70–230 mesh) and eluted with successively higher concentrations of methanol in methylene chloride ranging from 10 to 30%. The major fractions are pooled together and evaporated in vacuo, yielding 6.5 g of a solid which is recrystallized from ethanol, yielding 3 g of a yellow solid, M.P. 184°–186° C. NMR, IR and elemental analysis indicate the desired thiadiazole-1-oxide product.

EXAMPLE 14

PREPARATION OF 3-AMINO-4-[3-[6-(1-DIMETHYLAMINOINDANYLOXY)]PROPYLAMINO]-1,2,5-THIADIAZOLE-1-OXIDE

Step 1. 1-Dimethylamino-6-methoxy-1,2-indene.

Titanium tetrachloride (11.5 g) in toluene (50 ml) is added over a period of 20 minutes to a stirred solution of 6-methoxy-1-indanone (19.6 g), anhydrous dimethylamine (32 g) in anhydrous toluene (350 ml) under an atmosphere of $N_2$, while maintaining a temperature of less than 9° C. After the addition is complete, the reaction mixture is a light green slurry, which is stirred at RT for 3 hours, filtered, and the filtrate evaporated in vacuo, yielding 23.2 g of a green oil. NMR indicates that 80–85% of the oil is the desired eneamine, which is used without further treatment in the next step.

Step 2. 1-Dimethylamino-6-methoxy indan.

A solution of anhydrous HCl (4.3 g) in THF (40 ml) is added to a stirred solution of the indene obtained in the previous step (23.0 g) in anhydrous THF (350 ml) under an atmosphere of $N_2$. Sodium cyanoborohydride (4.32 g) in methanol (75 ml) is added to the stirred reaction mixture over a period of 15 minutes, and the reaction mixture is stirred at RT under $N_2$ for an additional 4 hours. Nitrogen is vigorously bubbled through the reaction mixture for several minutes, after which it is evaporated in vacuo and the residue partitioned between methylene chloride and aqueous base. The layers are separated and the aqueous layer extracted with methylene chloride. The combined methylene chloride fractions are washed with $H_2O$ and stirred with 5% aqueous HCl. The combined acidic aqueous fractions are washed with methylene chloride and then made strongly alkaline with 50% sodium hydroxide solution, resulting in an oily precipitate. The precipitate is extracted with methylene chloride and the methylene chloride extract washed with saturated sodium chloride, dried over sodium sulfate, filtered and the filtrate evaporated in vacuo, giving 14.9 g of a brown oil, identified as the desired product by NMR analysis. This oil is used without further treatment for the next step.

Step 3. 1-Dimethylamino-6-hydroxy indan.

A mixture of 1-dimethylamino-6-methoxy indan (14.6 g) and 48% hydrobromic acid (140 ml) in glacial acetic (140 ml) is refluxed with stirring under $N_2$ for 3 hours. The cooled reaction mixture is poured into crushed ice and the pH adjusted to about 8–9 with 50% sodium hydroxide solution, resulting in the formation of an oil and a dark solid precipitate. The aqueous mixture is extracted with methylene chloride, the methylene chloride extract washed with $H_2O$ and saturated sodium chloride solution, dried over sodium sulfate, filtered and the filtrate evaporated in vacuo, resulting in 9.6 g of a brown solid. The brown solid is dissolved in boiling toluene and the slightly cloudy supernatant decanted from a dark oily material. The toluene solution is cooled resulting in the formation of a precipitate which is filtered and allowed to air dry, resulting in 6.85 g of a beige crystalline solid, 44° C. NMR indicates this to be the desired M.P. 141°–144° C. NMR indicates this to be the desired product, which is used without further treatment for the next reaction.

Step 4. 1-Dimethylamino-6-(3-N-phthalimidopropoxy) indan.

Potassium t-butoxide (4.3 g) is added to a stirred solution of the phenol obtained in the previous step (6.1 g) in dimethylformamide (60 ml). N-(3-bromopropyl) phthalimide (18.5 g) is added to the stirred solution, resulting in the formation of a brown suspension. The reaction mixture is stirred at RT for 48 hours. The reaction mixture is partitioned between ether and $H_2O$, the layers separated and the aqueous layer made more basic with 50% sodium hydroxide solution, and subsequently extracted with additional ether. The combined ether layers are washed with $H_2O$ and stirred with 5% aqueous HCl. The ether layer is again washed with 5% aqueous HCl and the combined aqueous layers washed with methylene chloride. The acidic phase is made strongly alkaline with 50% sodium hydroxide solution and extracted with methylene chloride. The methylene chloride is washed with aqueous base and $H_2O$, dried over sodium sulfate, filtered and evaporated in vacuo, yielding 5.9 g of an amber oil, identified by NMR and IR analysis to be the desired phthalimido product.

Step 5. 6-(3-Aminopropoxy)-1-dimethylamino indan.

85% hydrazine hydrate solution (1.1 ml) is added to a suspension of 6-(3-N-phthalimidopropoxy)-1-dimethylamino indan (5.8 g) in absolute ethanol (55 ml). The reaction mixture is stirred at reflux for 3 hours, allowed to cool, and the mixture filtered. The filtered solid is washed with ethanol, the filtrate evaporated in vacuo and the residue triturated with 5% aqueous hydrochloric acid. The triturated solid is filtered and washed with 5% HCl. The filtrate is washed with ether and made strongly alkaline with 50% sodium hydroxide solution, resulting in the formation of an oily precipitate. The oil is extracted with diethyl ether and the ether washed with saturated sodium chloride solution. The combined aqueous layers are back-extracted with methylene chloride. The combined organic extracts are dried over sodium sulfate, filtered and the filtrate evaporated affording 3.2 g of an amber oil, identified by NMR to be the desired amine product.

Step 6. 3-Amino-4-[3-[6-(1-dimethylaminoindanyloxy)]-propylamino]-1,2,5-thiadiazole-1-oxide.

6-(3-Aminopropoxy)-1-dimethylamino indan (3.1 g) in methanol (60 ml) is added over a period of 90 minutes to a stirred solution of 3,4-dimethoxy-1,2,5-thiadiazole-1-oxide (2.15 g) in methanol (200 ml) under an atmosphere of $N_2$, while maintaining the reaction temperature at about 5° C. The reaction mixture is stirred for 2½ hours, after which anhydrous ammonia (20 g) is bubbled into the reaction mixture over a period of 5 minutes. The reaction mixture is allowed to react RT and stirred under $N_2$ overnight. The reaction mixture is evaporated in vacuo, affording 4.8 g of a foam which is dissolved in 5% methanol and methylene chloride and stirred at RT for 2 hours. The resulting cloudy solution is filtered and evaporated in vacuo. The residue is dissolved in 10% methanol in methylene chloride, placed on a silica gel column (150 g; 70-230 mesh) and eluted with successive concentrations of methanol in methylene chloride (10% to 40% methanol). The major fractions are pooled and evaporated in vacuo, resulting in 3.5 g of a foam, which is stirred in diethyl ether overnight. The resulting suspension is filtered and the solid washed with ether and dried at 60° C. at 5 mm Hg for 3 hours, resulting in 3.1 g of a white powder, M.P. 160°-162° C. (dec). NMR, IR and elemental analysis indicate that the white powder is the desired thiadiazole product.

EXAMPLE 15

THE PREPARATION OF 3-AMINO-5-[3-[4-(1-PIPERIDINYLINDANYLOXY)]-PROPYLAMINO]-1-METHYL-1H-1,2,4-TRIAZOLE

Step 1. 4-Methoxy-1-indanone.

Methyl iodide (69 ml) is added dropwise over a period of 15 minutes to a stirred mixture of 4-hydroxy-1-indanone (150 g) and anhydrous potassium carbonate (154 g) dissolved in DMF (1.5 liter) cooled to 0° C. under nitrogen. The reaction mixture is stirred at RT for 24 hours and partitioned between methylene chloride and water. The methylene chloride fraction is washed with water and 2% aqueous NaOH and dried over $Na_2SO_4$. The dried extract is filtered, concentrated in vacuo and the residue dissolved in hot methanol which upon cooling forms a precipitate. The precipitate is filtered and recrystallized from methanol yielding the methoxy product as a solid, M.P. 104°-106° C.

Step 2. 1-Hydroxy-4-methoxyindan.

Sodium borohydride (9.65 g) is added over a period of 15 minutes to a stirred suspension of 4-methoxy-1-indanone (127.3 g) in ethanol (650 ml) at a temperature of 24° C. under nitrogen. The reaction mixture is refluxed for 2 hours, cooled and glacial acetic acid (15 ml) added. The resulting mixture is concentrated in vacuo and the residue partitioned between ether and water. The ether extract is washed with water, saturated sodium bicarbonate, saturated salt, dried over $Na_2SO_4$, filtered and concentrated in vacuo yielding the hydroxy compound as a solid, M.P. 77.5°-79.5° C.

Step 3. 1-Chloro-4-methoxyindan.

Anhydrous hydrogen chloride is bubbled for 3 hours into a stirred mixture of 1-hydroxy-4-methoxyindan (117.9 g), calcium chloride (120 g, 4-20 mesh), and anhydrous toluene (2 l). The reaction mixture is decanted and filtered and the filtrate and supernatant evaporated yielding a brown oil which is used in the next step without further purification.

Step 4. 4-Methoxy-1-piperidinylindan.

A solution of 1-chloro-4-methoxyindan (from Step 3) in chloroform (130 ml) is added over a period of ten minutes to a stirred mixture of piperidine (284 ml) in chloroform (400 ml) under nitrogen. The reaction mixture is heated to reflux for six hours and allowed to stand at RT overnight. The mixture is treated with 10% aqueous HCl and the organic layer separated. The aqueous layer is extracted with methylene chloride and the combined organic extracts washed with 10% aqueous HCl. The organic layer is evaporated in vacuo and the residue partitioned between 5% aqueous HCl and ether. The combined aqueous fraction is washed with ether, made alkaline, and the alkaline layer extracted with ether. The ether extract is washed, dried and concentrated in vacuo yielding the piperidine indan as an oil.

Step 5. 4-Hydroxy-1-piperidinylindan.

Hydrobromic acid (47-49%, 750 ml) is added to a stirred solution of the 4-methoxy-1-piperidinylindan (75 g) in glacial acetic acid (750 ml) under nitrogen. The mixture is refluxed for four hours, allowed to cool and poured into crushed ice and water. The pH of the ice mixture is adjusted to about 9 and the aqueous mixture extracted with methylene chloride. The methylene chloride extract is washed with water thereby forming a precipitate which is filtered and the solid dried. The methylene chloride layer is evaporated yielding an oil. The solid is dissolved in acetonitrile and treated with charcoal. The oil is treated with charcoal and dissolved in acetonitrile. Both dissolved materials are recrystallized from acetonitrile yielding the desired product, M.P. 134.5°-136.5° C.

Step 6. 4-(3-Bromopropyl)-1-piperidinylindan.

Potassium hydroxide (53 g, 87%) is added over a period of 1 hour 15 min to a stirred suspension of 4-hydroxy-1-piperidinylindan (30 g), and tetrabutylammonium chloride (4.1 g) in 1,3-dibromopropane (140 ml) and the resulting mixture stirred at RT under nitrogen for two hours. The reaction mixture is partitioned between ice-water and ether and the aqueous layer separated and extracted with ether. The combined organic extracts are washed with water and ice cold 5% aqueous HCl forming a precipitate which is filtered and washed with ether. The acidic fraction is made strongly alkaline forming an oil precipitate which is extracted into ether. The combined ether layers are washed, dried over $Na_2SO_4$, filtered and concentrated in vacuo yielding the desired product as an oil which is used in the next step without further treatment.

Step 7. 4-(3-Azidopropoxy)-1-piperidinylindan.

Sodium azide (7.84 g) is added to a stirred solution of 3-bromopropoxy-1-piperidinylindan (40 g from Step 6 above) in ethanol/water (800 ml/80 ml) and the mixture heated to reflux for 24 hours. The reaction mixture is partitioned between water and methylene chloride and the organic layer separated, washed, dried, filtered and evaporated in vacuo yielding the desired azide indan as an oil.

Step 8. 4-(3-Aminopropoxy)-1-piperidinylindan.

A solution of the azido indan (38 g) (of Step 7 above) in ether (250 ml) is added over a period of 30 min to a suspension of LAH in anhydrous ether (1.5 l) stirred under nitrogen. The mixture is refluxed for about 1.5 hours then cooled and 6 ml $H_2O$ added. Aqueous NaOH (15% solution, 6 ml) is added followed by $H_2O$ (18 ml) and stirring continued for about 1.5 hours. The reaction mixture is filtered, the solid washed with ether and the filtrate dried over $Na_2SO_4$, filtered and concentrated in vacuo. The residue is dissolved in methylene chloride, dried, filtered and evaporated yielding the desired product as an oil.

Step 9. 3-Amino-5-[3-[4-(1-piperidinylindanyloxy)-propylamino]-1-methyl-1H-1,2,4-triazole.

A mixture of 5-(3-aminopropoxy)-1-(1-piperidinyl)indan (4.7 g) and methyl-N-cyano-1-methyl-2-(phenylmethylene)hydrazinecarboximidothioate (3.98 g) is stirred neat under vacuum at 70°–78° C. for about 3.5 hours. The reaction mixture is allowed to cool and 100 ml of a 5% aqueous HCl/acetone (60:40) solution is added dropwise to the reaction mixture over a period of one hour. 100 ml of water is added to the mixture which is washed with ether. The aqueous mixture is alkalinized with NaOH solution and the resulting oil extracted with ethyl acetate. The organic extract is washed, dried over $Na_2SO_4$, filtered and the filtrate evaporated yielding a solid which is recrystallized from hot acetonitrile and dried under vacuum giving the desired product, M.P. 135°–136.5° C.

EXAMPLE 16

THE PREPARATION OF N-[3-[4-(1-PIPERIDINYLINDANYLOXY)]-PROPYL]-1,2-BENZISOTHIAZOL-3-AMINE-1,1-DIOXIDE

A solution of 3-chlorobenzoisothiazole-1,1-dioxide (2.42 g) in chloroform (100 ml) is added over a period of about one hour to a refluxing solution of 5-(3-aminopropoxy)-1-(1-piperidinyl)-indan (3.0 g) in chloroform (300 ml) under nitrogen. The reaction mixture is refluxed for an additional hour, evaporated in vacuo, and the residue is triturated with a mixture of hot ethanol and triethylamine. The precipitate is filtered, the filtrate evaporated in vacuo and the resultant solid is dissolved in methanol and chromatographed on silica gel (100 g, 230–400 mesh) eluting with methanol. The fractions showing $R_f=0.24$ by tlc are combined and evaporated. The residue is triturated in ethyl acetate, filtered and the solid dried under vacuum yielding the desired product as a solid, M.P. 209°–212° C.

The following compounds may be prepared by analagous reaction pathways utilizing the corresponding starting materials and reagents.

3-Amino-5-[3-[5-(1-pyrrolidinyl-1,2,3,4-tetrahydronaphthyloxy)]propylamino]-1-methyl-1H-1,2,4-triazole; M.P.=177°–179° C.

3-Amino-5-[3-[4-(1-diethylaminoindanyloxy)]-propylamino]-1-methyl-1H-1,2,4-triazole.¼ $H_2O$; M.P.=142°–144° C.

3-Amino-5-[3-[6-(1-piperidinylindanyloxy)]propyl amino]-1-methyl-1H-1,2,4-triazole; M.P.=141°–144° C.

3-Amino-5-[4-[5-(1-piperidinyl-1,2,3,4-tetrahydronaphthyloxy)]butylamino]-1-methyl-1H-1,2,4-triazole M.P.=115°–118° C.

3-Amino-4-[3-[6-(1-piperidinylindanyloxy)]-propylamino]-1,2,5-thiadiazole-1-oxide; M.P.=184°–186° C.

1-Cyano-3-[3-[5-(1-piperidinyl-1,2,3,4-tetrahydronaphthyloxy)]propyl]-2-methylpseudothiourea; M.P.=145°–146° C.

5-(2-Aminoethoxy)-1-piperidinyl-1,2,3,4-tetrahydronaphthalene; M.P.=89°–92° C.

1-Cyano-3-[3-[5-1-piperidinyl-1,2,3,4-tetrahydronaphthyloxy)] ethyl]-2-methylpseudothiourea; M.P.=185°–187° C.

3-Amino-5-[3-[5-(1-piperidinyl-1,2,3,4-tetrahydronaphthyloxy)]propylamino]-1-benzyl-1H-1,2,4-triazole; (glass).

3-Amino-5-[2-[5-(1-piperidinyl-1,2,3,4-tetrahydronaphthyloxy)]ethylamino-1-methyl-1H-1,2,4-triazole .¼ $H_2O$; M.P.=79°–81° C.

3-Amino-5-[3-[5-(1-piperidinyl-1,2,3,4-tetrahydronaphthyloxy)]propylamino]-1-ethyl-1H-1,2,4-triazole; M.P.=186°–187° C.

3-Amino-5-[2-[4-(1-piperidinylindanyloxy)]ethylamino]-1-methyl-1H-1,2,4-triazolemethanesulfonate; M.P.=204°–207° C.

3-Amino-4-[3-[4-(1-piperidinylindanyloxy)]-propylamino]-1,2,5-thiadiazole-1-oxide; M.P.=184°–187° C.

EXAMPLE 17

THE PREPARATION OF 1-AMINO-2-[3-[4-(1-1-PIPERIDINYLINDANYLOXY)]PROPYLAMINO]CYCLOBUTENE-3,4-DIONE

A solution of 5-(3-aminopropoxy)-1-1-piperidinylindan (3.82 g) in methanol (40 ml) is added to a stirred solution of 1,2-dimethoxy cyclobutene-3,4-dione (1.98 g) in methanol (40 ml) cooled in an ice bath under a nitrogen atmosphere. The reaction mixture is allowed to warm to RT, stirred at RT for 2 hours and cooled to ice bath temperature. An excess of anhydrous ammonia is bubbled into the reaction mixture which is allowed to warm to RT and stirred overnight at RT. The reaction mixture is filtered and the solid precipitate washed with methanol and ether, dried under vacuum and recrystallized from DMF. The crystalline product is dried at elevated temperature in vacuo yielding the desired product as a white powder, M.P. 240°–242° C. (dec).

EXAMPLE 18

THE PREPARATION OF 1-AMINO-2-[3-[5-[1-(1-PIPERIDINYL)-1,2,3,4-TETRAHYDRONAPHTHYLOXY]PROPYLAMINO]-CYCLOBUTENE-3,4-DIONE

A solution of 3-[5-(1-piperidinyl)-1,2,3,4-tetrahydronaphthyloxy]propylamine (3.69 g) in methanol (40 ml) is added dropwise to a stirred solution of 1,2-dimethoxy-cyclobutene-3,4-dione (1.8 g) in methanol (40 ml) cooled to 5° C. Excess anhydrous ammonia is bubbled into the cooled mixture for 5–10 min and stirring is continued at RT for about 18 hours. The reaction mixture is filtered, the solid washed with methanol and dried at 60° C. in vacuo, yielding the desired product, M.P. 242°–245° C. (dec) (discolors at about 220° C.)

EXAMPLE 19

THE PREPARATION OF 3-HYDROXYMETHYL-5-[3-[5-[1-(1-PIPERIDINYL)-1,2,3,4-TETRAHYDRONAPH-THYLOXY]PROPYLAMINO]]-1-METHYL-1H-1,2,4-TRIAZOLE

Step 1. 1-Acetoxyacetyl-2-methyl-2-[phenylmethyleneamino]-3-[3-[5-[1-(1-piperidinyl)-1,2,3,4-tetrahydronaphthyoxy]]propyl]guanidine.

A neat mixture of Methyl-N-[2-(acetyloxy)acetyl]-1-methyl-2-(phenylmethylene)hydrazinecarboximidothioate (6.39 g) and 5-(3-aminopropoxy)-1-piperidinyl-1,2,3,4-tetrahydronaphthalene (6.0 g) is heated under house vacuum at about 67° C. for about 12 hours. The reaction mixture is dissolved in hot ethyl acetate and concentrated in vacuo forming a precipitate. The precipitate is filtered and the filtrate evaporated, the residue dissolved in methylene chloride and chromatographed (silica gel: 230–400 mesh) eluting with methylene chloride and methanol. The fractions eluted with 5% MeOH/CH2Cl2 were combined and concentrated affording the desired product as an oil which is used in the next step without further purification.

Step 2. 3-Hydroxymethyl-5-[3-[5-[1-piperidinyl-1,2,3,4-tetrahydronaphthyloxy]]propylamino]-1-methyl-1H-1,2,4-triazole.

A mixture of 1-acetoxyacetyl-2-methyl-2-[phenylmethyleneamino]-3-[3-[5-(1-piperidinyl-1,2,3,4-tetrahydronaphthyloxy)propyl]guanidine (7.5 g), aqueous hydrochloric acid (12 N, 250 ml) and absolute ethanol (30 ml) is stirred at RT for about 20 hours. The reaction mixture is washed with ether and the aqueous layer neutralized to pH 7, treated with 10.3 ml of 4 M KOH, diluted with ethanol (30 ml) and stirred for 35 min. The ethanol in the reaction mixture is evaporated in vacuo and the aqueous solution extracted with ethyl acetate. The organic extract is dried over MgSO4, filtered and concentrated in vacuo forming a solid. The solid is stirred with acetonitrile, filtered and the filtered solid dissolved in hot acetonitrile. Upon cooling a precipitate forms which is filtered, dissolved in methanol and chromatographed (silica gel, 230–400 mesh). The eluted fractions were combined, concentrated and recrystallized from acetonitrile affording the desired triazole, M.P. 150°–153° C.

EXAMPLE 20

THE PREPARATION OF 3-HYDROXYMETHYL-5-[3-[4-[1-PIPERIDINYLINDANYLOXY]]-PROPYLAMINO]-1-METHYL-1H-1,2,4-TRIAZOLE

Step 1. 1-Acetoxyacetyl-2-methyl-2-[phenylmethyleneamino]-3-[3-[4-(1-piperidinylindanyloxy)-propyl]guanidine.

A neat mixture of methyl-N-[2-(acetyloxy)acetyl]-1-methyl-2-(phenylmethylene)hydrazinecarboximidothioate (6.7 g) and 4-(3-aminopropoxy)-1-piperidinylindan (6.0 g) is heated to 65° C. under house vacuum for about 18 hours. Boiling ethyl acetate (70 ml) is added to the heated mixture and the mixture stirred. The mixture is allowed to cool forming a precipitate which is filtered and the filtrate is concentrated in vacuo. The residue is triturated with ether forming a precipitate which is filtered. The filtrate is concentrated in vacuo yielding the desired product as an oil which is used in the next step without further purification.

Step 2. 3-Hydroxymethyl-5-[3-[4-[1-piperidinylindanyloxy]]propylamino]-1-methyl-1H-1,2,4-triazole.

A mixture of 1-acetoxyacetyl-2-methyl-2-[phenylmethyleneamino]-3-[3-[4-(1-piperidinylindanyloxy)-propyl]guanidine (11.7 g), aqueous hydrochloric acid (12N, 250 ml) and absolute ethanol (45 ml) is stirred at RT for about 20 hours. The reaction mixture is washed with ether and the aqueous layer neutralized to pH 7, treated with 16 ml of 4 M KOH, diluted with ethanol (45 ml) and stirred for an additional 1.5 hour. The reaction mixture is concentrated in vacuo and the aqueous concentrate extracted with ethyl acetate, the extract dried over MgSO4, filtered and concentrated in vacuo. The residue is dissolved in methanol and chromatographed (silica gel, 230–400 mesh) eluting with methanol. The eluted fractions are combined and concentrated in vacuo to an amber oil, which is triturated with anhydrous ether to give the desired triazole as a white solid, M.P. 116°–119° C.

EXAMPLE 21

THE PREPARATION OF 3-(3-AMINOPROPOXY)-1-(PIPERIDINYLMETHYL)BENZOCYCLOBUTENE

Step 1. α-Cyano-4-methoxycinnamic acid.

A stirred mixture of p-anisaldehyde (60.7 ml), ammonium acetate (7.5 g), cyanoacetic acid (42.5 g), pyridone (70 ml) in toluene (390 ml) is refluxed using a Dean Stark trap until about 9 ml of water is collected. The reaction mixture is cooled and the solid precipitate filtered and stirred with 10% aqeuous HCL. The solid is filtered and recrystallized from methanol yielding the desired product.

Step 2. α-Cyano-β-(4-methoxyphenyl)propionic acid.

Sodium borohydride (30.2 g) is added portionwise over a period of 2 hours to a stirred mixture of α-cyano-4-methoxycinnamic acid (52.5 g) in aqueous saturated NaHCO3 (200 ml) and methanol (600 ml) cooled to about 15° C. The reaction mixture is allowed to warm to RT, stirred at RT for 30 min and concentrated in vacuo. The residue is partitioned between water and ether and the aqeuous layer acidified and extracted with ether. The ether extract is washed, dried over Na2SO4, filtered and the filtrate evaporated in vacuo producing a liquid which is crystallized from toluene yielding the desired product as a solid, M.P. 94°–95° C.

Step 3. 4-Methoxyphenylpropionitrile.

A stirred solution of α-cyano-β(4-methoxyphenyl)-propionic acid (127.3 g) in DMF (280 ml) is heated to 150° C. for 5 hours. The reaction mixture is cooled, poured into a liter of water and extracted with ether. The ether extract is washed, dried over Na2SO4, filtered and the filtrate evaporated in vacuo yielding a liquid which upon distillation yields the decarboxylated product as a clear liquid, B.P. 115° C. (1 mm).

Step 4. 3-Bromo-4-methoxyphenylpropionitrile.

Bromine (21.4 ml) is added dropwise over a period of 1 hour to a stirred solution of 4-methoxyphenylpropionitrile (67.5 g) and sodium acetate (68.4 g) in glacial acetic acid (420 ml). The reaction mixture is stirred for an additional 30 minutes and partitioned between water and ether. The ether layer is washed with sodium carbonate solution, 10% aqueous NaOH, saturated salt, dried over Na2SO4 and filtered. The filtrate is evaporated in vacuo yielding the desired product, B.P. 155°–158° C. (4 mm).

Step 5. 1-Cyano-5-methoxybenzocyclobutene.

3-Bromo-4-methoxyphenylpropionitrile (54.28 g) is added dropwise over a period of about 20 minutes to a stirred suspension of sodium amide (37.1 g) in liquid ammonia (250 ml) cooled to about −33° C. under nitrogen. The reaction mixture is refluxed for 3 hours after which ammonium nitrate (54.3 g) is added slowly to the mixture. The ammonia is allowed to evaporate overnight and the residue partitioned between water and methylene chloride. The organic fraction is washed with 5% HCl, saturated NaCl, dried over $Na_2SO_4$, filtered and the filtrate evaporated in vacuo yielding a liquid which is chromatographed (silica gel; 300 g; Hex-/Ethyl Acetate 3:1) affording the desired product as a clear liquid.

Step 6. 5-Methoxybenzocyclobutene-1-carboxylic acid.

1-Cyano-5-methoxybenzocyclobutene (29 g) is stirred with saturated KOH in ethanol (180 ml) for about 12 hours under nitrogen at RT. Water (60 ml) is added to the reaction mixture which is refluxed for about 3 hours. The mixture is cooled to RT, diluted with water, washed with ether and the aqueous layer acidified forming an oil. The oil is dissolved in ether and the ethereal solution washed, dried over $Na_2SO_4$, filtered and evaporated in vacuo affording the desired product as an oil.

Step 7. 5-Methoxy-1-hydroxymethylbenzocyclobutene.

A solution of 5-methoxybenzocyclobutene-1-carboxylic acid (32.0 g) in ether (1.2 l) is added dropwise to a stirred suspension of LAH (15.5 g) in ether (650 ml) under nitrogen. The reaction mixture is stirred at RT for 4 hours, after which, water (15.5 ml), 15% NaOH (15.5 ml) and a second portion of water added (46 ml) sequentially to the reaction mixture resulting in the formation of a precipitate. The ethereal layer is filtered, dried over $Na_2SO_4$, filtered and concentrated in vacuo yielding the desired product as an oil.

Step 8. 5-Methoxy-1-hydroxymethylbenzocyclobutene mesylate.

Methane sulphonyl chloride (13.4 ml) is added dropwise to a stirred solution of 5-methoxy-1-hydroxymethyl benzocyclobutene (26 g) and triethylamine (26.5 ml) in methylene chloride (670 ml) cooled to 0° C. under nitrogen. The reaction mixture is allowed to warm to RT, stirred for 2 hours at RT, washed with water and saturated salt, dried over $Na_2SO_4$, and filtered. The filtrate is concentrated in vacuo yielding the desired product as a liquid.

Step 9. N-(5-Methoxy-1-piperidinylomethyl-benzocyclobutene.

A solution of 5-methyl-1-hydroxymethylbenzocyclobutene mesylate (38 g) and piperidine (45 ml) in toluene (180 ml) is refluxed under nitrogen for about 12 hours. The reaction mixture is filtered and the filtrate is evaporated in vacuo leaving a liquid residue which is used without further purification in the next step.

Step 10. 5-Hydroxy-1-(1-piperidinylmethyl)-benzocyclobutane.

A solution of N-(5-methoxy-1-benzocyclobutenylmethyl)piperidine (0.75 g), trimethylsilyliodide (0.6 ml) in chloroform (1.6 ml) is stirred for about 18 hours under nitrogen at about 50° C.

Methanol is added to the reaction mixture resulting in the formation of a precipitate which is filtered and the filtrate concentrated in vacuo to a red oil. The oil is partitioned between ether and saturated aqueous sodium bicarbonate. The layers are separated and the aqueous layer washed with ether. The ether extracts are combined, washed with saturated salt, dried over $Na_2SO_4$, filtered and the filtrate evaporated affording the desired phenolic compound as a solid.

Step 11. 5-(3-Bromopropoxy)-1-(1-piperidinylmethyl)-Benzocyclobutene.

Potassium hydroxide (1.5 g, 10%) is added over a period of 1 hour 15 min to a stirred suspension of 3-hydroxy-1-(1-piperidinylmethyl)benzocyclobutene (1.0 g), and tetrabutylammonium chloride (0.13 g) in 1,3-dibromopropane (4.6 ml) and the resulting mixture stirred at RT under nitrogen for two days. The reaction mixture is partitioned between ice-water and ether and the aqueous layer separated and extracted with ether. The combined organic extract is washed with water, ice cold 5% aqueous HCl thereby forming a precipitate which is filtered and washed with ether. The acidic layer is alkalized forming an oily precipitate which is taken up in ether. The combined ether fractions are washed with water, dried over $Na_2SO_4$, filtered and concentrated in vacuo yielding the desired product as an oil which is used in the next step without further purification.

Step 12. 5-(3-Azidopropoxy)-1-(1-piperidinylmethyl)-benzocyclobutene.

Sodium azide (0.8 g) is added to a stirred solution of 5-(3-aminopropoxy)-1-(1-piperidinylmethyl)benzocyclobutene (0.8 g) (from Step 11 above) in ethanol/water (16 ml/1.6 ml) and the mixture heated to reflux for 24 hours. The reaction mixture is cooled and partitioned between water and methylene chloride. The organic layer is separated, washed with water, dried over $Na_2SO_4$, filtered and concentrated in vacuo, yielding the desired azido compound as an oil.

Step 13. 5-(3-Aminopropoxy)-1-(1-piperidinylmethyl)-benzocyclobutene.

A solution of the azido cyclobutene (0.7 g) (of Step 12 above) in ether (2.5 ml) is added over a period of about 30 min to a suspension of 0.15 g LAH in anhydrous ether (30 ml) stirred under nitrogen. The mixture is refluxed for about 1.5 hours and cooled. Water (0.15 ml), aqueous NaOH (15% solution, 0.15 ml) and water (0.45 ml) are added to the reaction mixture and stirring continued for about one hour. The mixture is filtered, the solid washed with ether and the filtrate dried over $Na_2SO_4$. The dried ether extract is filtered, concentrated in vacuo, and the residue is dissolved in methylene chloride, dried, filtered and concentrated yielding the desired product as an oil.

EXAMPLE 22

The Preparation of 3-(3-aminopropoxy)-1-(1-piperidinylmethylbenzocyclobutene

Step 1. 4-(3-Chloropropoxy)-1-indanone.

1-Bromo-3-chloropropane (17.3 g) is added to a stirred mixture of 4-hydroxyindanone (14.8 g), potassium carbonate (15.3 g) in DMF/water (150 ml/50 ml) and the reaction mixture stirred at RT for about 4 days. The reaction mixture is partitioned between water and methylene chloride and the organic layer is separated, dried, filtered and evaporated, affording a residue which is chromatographed on a silica gel column to yield the desired product as a white solid.

Step 2. 4-(3-Chloropropoxy)-2-oxime-1-indanone.

12.5 g of n-butyl nitrite is added to a stirred solution of 4-(3-chloropropoxy)-1-indanone (17.6 g) and hydrochloric acid (12N, 39.2 ml) in methoxyethanol (315 ml) and the mixture stirred at RT for 2 hours. The reaction mixture is poured into water, cooled to 0° C. in an ice bath resulting in the formation of a precipitate which is filtered, washed with water and dried yielding the desired oxime product as a yellow crystalline solid.

Step 3. 3-(Chloropropoxy)-2-diazo-1-indanone.

Ammonium hydroxide (8.74 ml, 15N) is added to a stirred mixture of 4-(3-chloropropoxy)-2-oxime-1-indanone (16.6 g) and sodium hydroxide (2.6 g) in water (500 ml) at 2° C. Sodium hypochlorite (218 ml, 5.25% aqueous solution) is added slowly to the reaction mixture maintained at about 2° C. and allowed to stand at RT for about 4 hours. The reaction mixture is filtered and the solid washed with water. The solid is dissolved in methylene chloride, filtered, dried over $Na_2SO_4$, and evaporated in vacuo resulting in the desired product as a solid.

Step 4. 3-(3-Chloropropoxy)benzocyclobutene-1-carboxylic acid.

A solution of 3-(chloropropoxy)-2-diazo-1-indanone (11.4 g) and sodium bicarbonate (9.4 g) in a solvent mixture of THF (800 ml) and water (140 ml) is photolyzed for 63 hours. The THF is evaporated in vacuo and the aqueous remainder partitioned between water and methylene chloride. The aqueous layer is acidified with conc. HCl and extracted with methylene chloride. The methylene chloride extract is washed with saturated NaCl, dried over $Na_2SO_4$, filtered and concentrated in vacuo yielding the desired carboxylic acid as an oil.

Step 5. 3-(3-Chloropropoxy)-1-hydroxymethylbenzocyclobutene.

A solution of 3-(3-chloropropoxy)benzocyclobutene-1-carboxylic acid (2.6 g) in THF (25 ml) is added to a stirred suspension of LAH (0.9 g) in 40 ml of ether under nitrogen. The reaction mixture is stirred at RT for 4 hours, and quenched with water (0.9 ml), 15% NaOH solution (0.9 ml) and water (2.6 ml). The reaction mixture is filtered and the ether/THF evaporated in vacuo. The residue is extracted with methylene chloride, the organic extract dried over $Na_2SO_4$, filtered and the solvent evaporated in vacuo yielding the desired product as an oil.

Step 6. 3-(3-Chloropropoxy)-1-hydroxymethylbenzocyclobutene mesylate.

Methane sulfonylchloride (1.13 g) is added dropwise to a stirred solution of 3-(3-chloropropoxy)-1-hydroxymethylbenzocyclobutene (1.83 g) and triethylamine (1.58 ml) in methylene chloride (32 ml) at 5° C. under nitrogen. The reaction mixture is stirred at RT for about 2 hours, washed with water, saturated NaCl, dried over $Na_2SO_4$, filtered and evaporated in vacuo yielding the desired product as an oil.

Step 7. 3-(3-Chloropropoxy)-1-(1-piperidinylmethyl)-benzocyclobutene.

Piperidine (3.19 ml) is added to a solution of 3-(3-chloropropoxy)-1-hydroxymethylbenzocyclobutene mesylate (2.45 g) in toluene (32 ml) and the reaction mixture refluxed under nitrogen for about 12 hours. The reaction mixture is diluted with ethyl acetate and extracted with saturated $NaHCO_3$ followed by saturated NaCl. The organic extract is dried, filtered and concentrated yielding the crude product used in the next step.

Step 8. 3-(3-Azidopropoxy)-1-(1-piperidinylmethyl)-benzocyclobutene.

Sodium iodide (3 g) is added to a stirred solution of 3-(3-chloropropoxy)-1-(1-piperidinylmethyl)benzocyclobutene (0.87 g) in 12 ml of DMF. The reaction mixture is stirred under nitrogen for 12 hours, sodium azide (1.17 g) is added to this solution followed by water (1.2 ml). The resulting suspension is heated at 75° C. for 5 hours. The reaction mixture is partitioned between water and methylene chloride and the organic layer is separated, washed, dried, filtered and evaporated in vacuo yielding the azide product as an oil.

Step 9. 3-(3-Aminopropoxy)-1-(1-piperidinylmethyl)benzocyclobutene.

A solution of the azido benzocyclobutenylmethyl compound (0.8 g) (step 8 above) in THF (5.2 ml) is added over a period of 30 min to a suspension of LAH (0.125 g) in anhydrous ether (16.5 ml) stirred under nitrogen. The mixture is refluxed for about 2 hours and cooled. Water (0.125 ml), aqueous NaOH (15% solution, 0.125 ml) and water (3.75 ml) are added to the cooled mixture which is filtered. The solid is washed with ether and the filtrate dried over $Na_2SO_4$. The dried filtrate is filtered, evaporated in vacuo and chromatographed (silica gel) eluting with 1:1 ethyl acetate/MeOH. The pure fractions are combined and evaporated in vacuo yielding an oil. NMR analysis identifies the oil as the desired product.

EXAMPLE 23

The Preparation of
3-amino-5-[3-[3'-[[1-piperidinylmethyl]benzocyclobutenylyoxy]propylamino]]-1-methyl-1H-1,2,4-triazole 3-[3-Aminopropoxy]-1-piperidinylmethylbenzocyclobutene (1.5 g) and N-cyano-1-methyl-2-phenylmethylenehydrazinecarboximidethioic acid methyl ester are dissolved in $CH_2Cl_2$ and evaporated in vacuo. The neat mixture is heated to 70° C. for four hours and the resultant glass is dissolved in 5% aqueous HCl (30 ml)/acetone (20 ml) and washed with ether. The aqueous solution is made alkaline resulting in a yellow oil which is taken up in ethyl acetate, washed with saturated salt, dried over $Na_2SO_4$, filtered and evaporated in vacuo to a yellow oil which is chromatographed (silica gel, 1/1:MeOH/EtOAc). The purified fractions are combined and evaporated to a glass which is triturated with ether yielding the desired product as a solid, M.P.=114°–116° C.

EXAMPLE 24

The Preparation of
5-(3-aminopropoxy)-1-piperidinylmethyl-1,2,3,4-tetrahydronaphthalene Step 1. 5-Methoxy-Spiro(1,2,3,4-tetrahydronaphthalene)-1,2'-oxirane.

Dimethylsulfoxide (500 ml) is added over a period of 15 minutes to a stirred mixture of sodium hydride (22.4 g) (60% dispersion oil removed by pet. ether) and trimethylsulfoxonium iodide (116 g) under nitrogen. The reaction mixture is stirred at RT for 1 hour. A solution of 5-methoxytetralone (75 g) in DMSO (350 ml) is added over a period of 15 min to the reaction mixture and stirred at RT for 2 hours, at 50°–55° C. for an additional hour and poured into water/crushed ice. The aqueous mixture is extracted with ether and the ether extract washed, dried over $Na_2SO_4$, filtered and the filtrate evaporated in vacuo yielding the desired product as an oil.

Step 2. 1-Hydroxy-5-methoxy-1-piperidinylmethyl-1,2,3,4-tetrahydronaphthalene.

A solution of 5-methoxy-spiro (1,2,3,4-tetrahydronaphthalene)-1,2'-oxirane (73 g) and piperidine (49 g, distilled) in absolute ethanol (750 ml) is refluxed under nitrogen for 18 hours. The reaction mixture is evaporated in vacuo and the residue partitioned between ether and 5% aq. HCl. The acidic layer is separated and washed with ether, made strongly alkaline and the precipitated oil extracted with ether. The ethereal extract is washed, dried, filtered and the filtrate evaporated in vacuo yielding the desired product as an oil.

Step 3. 5-Methoxy-1-piperidinylmethyl-1,2-dihydronaphthalene.

The hydroxy compound of Step 2 (75 g) is dissolved in 20% (w/w) sulfuric acid (375 ml) and refluxed under nitrogen for 18 hours. The cooled mixture is poured into ice-water, extracted with ether and the aqueous layer made strongly alkaline. The precipitated oil is extracted into ether which is washed, dried, filtered and evaporated in vacuo yielding the desired product as an oil.

Step 4. 5-Methoxy-1-piperidinylmethyl-1,2,3,4-tetrahydronaphthalene.

5% Palladium on carbon (3.0 g) is added to a solution of 5-methoxy-1-piperidinylmethyl-1,2-dihydronaphthalene (63 g) in absolute ethanol (600 ml) and placed under H$_2$ at an initial pressure of 47 psi for 30 min. The reaction mixture is filtered and the filtrate evaporated in vacuo yielding the desired product as an oil.

Step 5. 5-Hydroxy-1-piperidinylmethyl-1,2,3,4-tetrahydronaphthalene.

A solution of the 5-methoxy compound from step 4 above (41 g), 47-49% hydrobromic acid (410 ml) in glacial acetic acid (410 ml) is stirred at reflux under nitrogen for 2.5 hours. The cooled reaction mixture is poured into ice/water, made alkaline and the pH adjusted until no more cloudiness appears. The resulting oil is extracted into ether, washed, dried, filtered and the filtrate evaporated in vacuo forming a solid residue which is recrystallized from hot acetonitrile yielding the desired product as a crystalline solid, M.P. = 129°-131° C.

Step 6. 5-(N-phthalimidopropoxy)-1-piperidinylmethyl-1,2,3,4-tetrahydronaphthalene.

Potassium t-butoxide (13.5 g) is added to a cooled solution of the phenol from Step 5 (27 g) in DMF (250 ml) and the mixture stirred for 5 min. N-(3-bromopropyl)pthalimide (58 g) is added to the stirred mixture and stirring continued at RT for 20 hours. The reaction mixture is partitioned between 2% NaOH solution and ethyl acetate. The ethyl acetate extract is stirred with 5% aqueous HCl forming a solid. The solid is filtered and the aqueous layer combined with the solid and made strongly alkaline. The resulting oil is extracted with ethyl acetate and the extract washed, dried, filtered and evaporated in vacuo to an oil which is dissolved in isopropanol forming a precipitate. The precipitate is filtered, dried and recrystallized from isopropanol yielding the desired product as a crystalline solid, M.P. = 76°-77.5° C.

Step 7. 5-(3-aminopropoxy)-1-piperidinylmethyl-1,2,3,4-tetrahydronaphthalene.

Hydrazine monohydrate (3.5 ml) is added to a stirred suspension of the N-pthalimido compound (25.7 g) in absolute ethanol (250 ml) and refluxed for three hours. The mixture is stirred at RT for one hour, filtered and the filtrate evaporated in vacuo. The residue and solid precipitate are combined and stirred with ice cold 5% HCl for 30 min. The suspension is filtered and the aqueous filtrate made strongly alkaline. The alkaline solution is extracted with ether and the extract dried, filtered and the filtrate evaporated in vacuo yielding the desired product as an oil.

The following compounds are prepared from the amino propoxy compound of Step 7 above utilizing reaction conditions analagous to those described in the foregoing examples.

3-Amino-5-[3-[5-(1-piperidinylmethyl-1,2,3,4-tetrahydronaphthyloxy)]propylamino]-1-methyl-1H-1,2,4-triazole; M.P. = 147°-8° C.

1-Cyano-2-methyl-3-[3-[5-(1-piperidinylmethyl)-1,2,3,4-tetrahydronaphthyloxy)]propyl]pseudothiourea; M.P. = 111°-113° C.

1-Amino-2-[3-[5-(1-piperidinylmethyl-1,2,3,4-tetrahydronaphthyloxy)]propylamino]cyclobutene-3,4-dione; M.P. = 241°-245° C. (dec).

EXAMPLE 25

Resolution of Enantiomers

Step 1. Resolution of S(+) and R(−) isomers of 5-methoxy-1-piperidinyl-1,2,3,4-tetrahydronapthalene.

Resolution of the racemic mixture of (+) 5-methoxy-1-piperidinyl-1,2,3,4-tetrahydronapthalene is accomplished by forming the diastereomeric salts thereof utilizing (+)-Dibenzoyl-D-tartaric acid and (−)-Dibenzoyl-L-tartaric acid. 95% EtOH is used as the recrystallization solvent. The melting points and specific rotations for the resolved diastereomeric salts are listed below.

(A) Salt of (−)5-methoxy-1-piperidinyl-1,2,3,4-tetrahydronapthalene.
M.P = 151.5°-152° C.
$[\alpha]_D^{RT} = -92.41°$
(conc. = 1 g/100 ml MeOH)

(B) Salt of (+)5-methoxy-1-piperidinyl-1,2,3,4-tetrahydronapthalene.
M.P. = 153°-153.5° C.
$[\alpha]_D^{RT} = +94.68°$
(conc. = 1 g/100 ml)

The free bases are oils and have the following specific rotations:

from (A) above
$[\alpha]_D^{RT} = -103.52°$ (conc. = 1.5 g/100 ml CH$_2$Cl$_2$)
from (B) above
$[\alpha]_D^{RT} = +102.26°$.

The following enantiomers are prepared from the optically active 5-methoxy starting materials by the methods described herein above.

| | M.P. | $[\alpha]_D^{RT}$ | (CH$_2$Cl$_2$) |
|---|---|---|---|
| R(−)-5-hydroxy-1-piperidinyl-1,2,3,4-tetrahydronapthalene | 145°-146.5° C. | −113.51° | $\left(c = \frac{1 \text{ g}}{100 \text{ ml}}\right)$ |
| R(−)-5-(3-phthalimidopropoxy)-1-piperidinyl-1,2,3,4-tetrahydronapthalene | 63°-65° C. | −43.02° | $\left(c = \frac{0.8 \text{ g}}{100 \text{ ml}}\right)$ |
| R(−)-5-(3-aminopropoxy)-1-piperidinyl-1,2,3,4-tetrahydronapthlane | | −69.13° | $\left(c = \frac{0.37 \text{ g}}{100 \text{ ml}}\right)$ |

-continued

| | M.P. | $[\alpha]_D^{RT}$ | $(CH_2Cl_2)$ |
|---|---|---|---|
| R(−)-1-cyano-2-methyl-3-[3-[5-[1-piperidinyl-1,2,3,4-tetrahydronapthyloxy]-propyl]pseudothiourea | 123°–124° C. | −56.54° | $\left(c = \frac{0.82 \text{ g}}{100 \text{ ml}}\right)$ |
| R(−)-3-amino-5-[3-[5-(1-piperidinyl-1,2,3,4-tetrahydronapthyloxy)]propyl-amino]-1-methyl-1H—1,2,4-triazole | 155–157° C. | −57.09° | $\left(c = \frac{1 \text{ g}}{100 \text{ ml}}\right)$ |
| S(+)-5-hydroxy-1-piperidinyl-1,2,3,4-tetrahydronapthalene | 144.5°–146° C. | +115.82° | $\left(c = \frac{1 \text{ g}}{100 \text{ ml}}\right)$ |
| S(+)-5-(3-phthalimidopropoxy)-1-piperidinyl-1,2,3,4-tetrahydronapthalene | 82–83.5° C. | +49.95° | $\left(c = \frac{0.9 \text{ g}}{100 \text{ ml}}\right)$ |
| S(+)-5-(3-aminopropoxy)-1-piperidinyl-1,2,3,4-tetrahydronapthlane | — | +80.26° | $\left(c = \frac{0.43 \text{ g}}{100 \text{ ml}}\right)$ |
| S(+)-1-cyano-2-methyl-3-[3-[5-[1-piperidinyl-1,2,3,4-tetrahydronapthyloxy]]-propyl]pseudothiourea | 123.5–124.5° C. | +56.48° | $\left(c = \frac{0.8 \text{ g}}{100 \text{ ml}}\right)$ |
| S(+)-3-amino-5-[3-[5-(1-piperidinyl-1,2,3,4-tetrahydronapthyloxy)]propyl-amino]-1-methyl-1H—1,2,4-triazole | 155–157° C. | +56.00° | $\left(c = \frac{1 \text{ g}}{100 \text{ ml}}\right)$ |

Various tests in animals have been carried out to show the ability of the compounds of this invention to exhibit pharmacological responses that can be correlated with activity in humans. These tests involve such factors as the effect of the compounds of Formula I on gastric secretion and their $H_2$ antagonist and cytoprotective activity. It has been found that the compounds of this invention when tested in the above variety of situations show a marked activity.

One such test is the gastric secretion test. This test is carried out as follows: Shay rats are fasted for 4–8 hours, and water is given ad lib. The rats are selected at random and separated into groups of 10. The animals are treated intraduodenally (I.D.) with the test compounds or the vehicle immediately subsequent to the ligation of the stomach at the pyloric sphincter. The animals are sacrificed with chloroform at 4 hours post-drug administration, the stomach removed and its contents assayed for volume, pH and total acids.

A second gastric secretion test is carried out on the dog. This is outlined in the *Handbook of Physiology*, Section 6: Alimentary Canal, Volume II: Secretion. American Physiology Society, Washington, D.C., 1967.

It has been found that the compounds of this invention, when subjected to the above gastric secretion tests, display marked ability to decrease gastric volume and gastric acidity. These tests are known to correlate well with gastric activity in humans and are standard tests used to determine anti-secretory properties.

The compounds of Formula I have been found to be histamine $H_2$-receptor antagonists by the results obtained in the following $H_2$-antagonist tests.

A. Isolated Guinea Pig Atria

The $H_2$-receptor antagonist activity of the compounds of Formula I is measured by observing the beat rate response versus compound concentration in isolated guinea pig atria. A discussion of criteria to evaluate these dose-response curves may be found in, E. J. Ariens, G. A. J. vanOs, A. M. Simonis, and T. M. van Rossum, "A Molecular Approach to General Pharmacology", Sections 11A, 11B, and 111, *Molecular Pharmacology: The Mode of Action of Biologically Active Compound*. Vol. 1, Academic Press (1964).

1. Tissue Bath

A fifty ml jacketed tissue bath is maintained at 30° C. The bath consists of a Krebs-Henseleit buffer aerated with 95% $O_2$–5% $CO_2$, (pH 7.4). The buffer is prepared by mixing: 4 ml of an aqueous (distilled deionized) solution of $CaCl_2.2H_2O$ (0.37 g/ml); 4 ml of an aqueous (distilled deionized) solution of $MgSO_4.7H_2O$ (0.29 g/ml); 7.2 g of glucose; and, 2 liters of aqueous (distilled deionized) solution containing NaCl (28 g), $NaHCO_2$ (8.4 g), KCl (1.4 g) and $KH_2PO_4$ (0.6 g).

2. Preparation of Atria

Male albino guinea pigs (400–700 g, preferably 500–600 g) are killed by a blow to the back of the head and exsanguinated by cutting jugular veins and carotid arteries. The thoracic skin is opened from this neck cut and the rib cage exposed. Both sides of the rib cage and the diaphragm are cut and laid back, exposing the heart. The heart is removed by cutting through the vessels above and behind it while it is slightly elevated with forceps holding the ventricle tip. The heart is immediately placed in warm, aerated buffer and further dissected in a large petri dish of the same buffer. Since the pericardium is removed, it is possible to slip iris scissors between the atria and ventricles while holding the aorta and vessels with tweezers and cut off the atria. The atria are then dissected from any remaining tissue and vessels and suspended in the bath using small, curved taper-point needles formed into hooks and tied to an S-shaped hook and the L-shaped lower support with 00 silk.

A Beckman Type 9308 Strain Gauge Coupler connects a Beckman cardiotachometer to a Grass FT03C strain gauge supported in a rack and pinion clamp. The upper hook of the strain gauge is placed in the edge of the left atrium and the lower hook in the tip of the right atrium. The lower support is clamped in a femur clamp and the upper hook is suspended from the strain gauge lug. The strain gauge is raised until the resting tension on the tissue is 1 gram. The tissue is allowed to stabilize for about one hour with several buffer washings and tension adjustments before the addition of the test compounds.

3. Test Procedure

A control dose-response curve using cumulative, approximately tripling doses is obtained in all three running from 0.1 to 30.0M histamine (0.1, 0.3, 1.0, 3.0, etc.) In order to minimize volume changes when adding drugs to the bath, small volumes of concentrated solutions are used. It is convenient to make up a 0.5M solution and dilute it to give 50, 5 and 0.5 mM solutions.

Data recorded consists of the initial baseline rate and the stable plateau rate after each addition. Histamine is then washed out and the tissues are allowed to stabilize again near the initial baseline rate; this may take several rinses and 1 hr. The test compound is then added at the same cumulative doses and rates again recorded. If the compound behaves as an agonist and stimulates, then the dose is increased until the rate plateaus or the concentration is 1.0 mM. If, however, no agonistic activity is observed when the concentrations has reached 100M then its antagonistic activity is assessed by repeating the histamine curve without washing out the test compound. Reversibility of effect is assessed by attempting to wash out the test compound and/or histamine and repeat the histamine curve. Erratic or irregular beating or any other abnormal behavior at any time is noted. Calculations consist of the change in rate from base line and that change as a percentage of the maximum rate obtained in the initial control curve. The mean of those percentages (+SEM) is plotted as a function of agonist concentration (either histamine or test compound) to evaluate the type of response.

B. Lumen Perfused Rat Stomach—Effect on the Gastric Secretion

Male Sprague-Dawley rats weighing between 350 and 500 gm are housed individually according to standard animal husbandry procedures and are deprived of food twenty-four hours prior to testing. The rats are anesthetized by an intraperitoneal injection of 25% solution of urethane (0.5 to 0.7 ml/100 g of body weight). Once anesthetized, the trachea is exposed and cannulated with PE 100 tubing. The jugular vein is exposed and cannulated with PE 50 tubing bevelled at the tip. The abdomen is opened through a midline incision, and the esophagus is isolated excluding the vagus nerve. PE 190 tubing, with a flange on one end, is passed down the rat's mouth through the esophagus and into the stomach. The esophagus is tied off and the tubing checked to make sure that it is securely in the stomach. The duodenum is then identified and a small cut made about 1 cm below the pyloric sphincter. A piece of PE 320 tubing (flanged at one end) is inserted through the cut and into the stomach. It is secured firmly by tying a ligature around the pylorus. Using a 50 ml syringe, the stomach is flushed out with 0.4 mM NaOH through the esophageal tube until the perfusate emerging from the pyloric tube is clear. The animal is placed on a tilted table covered with a Gordon-Rupp water blanket Model 'K' to maintain the rat's body temperature at 30° C. The tube going into the esophagus is attached to a Sage Peristaltic Pump and 0.4 mN NaOH (pH 10.0) is perfused and collected in 30 ml beakers. The beakers are changed every 10 or 15 minutes and the pH of these samples are recorded. Once the pH has stabilized around 6.5-7.5, drugs that affect gastric secretion are given intravenously. The effectiveness of a compound is based on its ability to prevent a drop in pH initiated by a gastric stimulant, such as histamine. See, Ghosh, M. N. and Schild, H. O., *Brit. J. Pharmacol.*, 13: 54 (1958).

Compounds within the scope of Formula I have also been determined to exhibit anti-ulcer activity. The anti-ulcer properties of these compounds can be evaluated using an anti-ulcer assay in which aspirin or another nonsteroidal anti-inflammatory agent is used to induce gastric ulcers in the rat according to the following test procedure.

See, Corell, T., "Interaction of Salicylates and other Non-steroidal Anti-inflammatory Agents in Rats as Shown by Gastro-ulcerogenic and Anti-inflammatory Activities, and Plasma Concentrations", Acta. Pharmacology et. Toxicology, 45, 225-231 (1979).

Male Sprague-Dawley rats 140-170 g are housed according to standard animal husbandry procedures. The rats are fasted twenty-four hours prior to testing. On the test day, rats are divided into groups of 5 or 10, with one group serving as controls and receiving vehicle (for example, distilled water or a 0.1% Tween 80 solution). The test compounds, using logarithmic doses, are administered at a dose volume of 10 ml/kg. Thirty minutes post-drug, the rats are orally administered (10 ml/kg) aspirin or indomethacin suspended in 0.1% Tween 80 at a dose of 150.0 or 20.0 mg/kg, respectively. Four hours following indomethacin administration (five hours after aspirin administration) animals are sacrificed via cervical dislocation; their stomachs are removed, opened along the greater curvature, and gently rinsed and examined for lesions with a 10×magnifying glass; the following scale is employed:

| Grade | Description |
| --- | --- |
| 0 | No lesions |
| 1 | 5 lesions, all <2 mm |
| 2 | 5 lesions, at least 1 > 2 mm |
| 3 | 5-10 lesions, all <2 mm |
| 4 | 5-10 lesions, at least 1 > 2 mm |
| 5 | 10 lesions, all <2 mm |
| 6 | 10 lesions, at least 1 > 2 mm |
| 7 | Perforation |

The average ulcer severity (±S.E.) for each group of animals is calculated. The percent inhibition for each test compound is calculated as follows:

$$\% \text{ inhibition} = \frac{\text{Mean value for control} - \text{Mean value for experimental}}{\text{Mean value for control}} \times 100$$

The compounds of Formula I have also been determined to exhibit cytoprotective activity.

The cytoprotective effectiveness of the compounds of Formula I is evaluated according to the following test procedure.

Male Sprague-Dawley rats 150-200 g are housed according to standard animal husbandry procedures. The rats are fasted twenty-four hours prior to testing. On the test day, rats are divided into groups of 6, with one group serving as controls and receiving vehicle (for example, distilled water or a 0.5% Methocel solution). The test compounds, using logarithmically spaced doses, are administered at a dose volume of 5 ml/kg. Ten minutes post-drug, the rats are orally administered 1 ml of absolute alcohol, 0.2N NaOH (1 ml) or 0.6N HCl (1 ml), regardless of body weight. One hour after administration animals are sacrificed by cervical dislocation, their stomachs are removed, opened along the greater curvature, rinsed under running tap water and examined for lesions with a 2×-10× magnifying glass.

The reduction of lesion count, lesion severity score and ulcer index as compared to similar measurements made in the controls was expressed as a percentage. Measurement of statistical significance of the results was done by standard methods.

The average ulcer severity (±S.E.) for each group of animals is calculated. The percent inhibition for each test compound is calculated as follows:

$$\% \text{ inhibition} = \frac{\text{Mean value for control} - \text{Mean value for experimental}}{\text{Mean value for control}} \times 100$$

The results of the anti-secretory, anti-ulcer and cytoprotective assays, detailed above, establish the anti-secretory activity, the H₂-receptor antagonist activity, the anti-ulcer activity, the cytoprotective activity, and the utility of the compounds of the present invention in the treatment of peptic ulcers in mammals, including humans. These compounds both aid in the healing of such ulcers and also prevent their formation.

The most preferred anti-secretory and anti-ulcer compound within the scope of Formula I is 3-amino-5-[3-[4-[1-(1-piperidinyl)indanyloxy]]propylamino]-1-methyl-1H-1,2,4-triazole and the pharmaceutically acceptable salts thereof.

Another preferred compound is 3-amino-5-[3-[5-[1-(1-piperidinyl)-1,2,3,4-tetrahydronaphthyloxy]]-propylamino]-1-methyl-1H-1,2,4-triazole and the pharmaceutically acceptable salts thereof.

The most preferred class of compound according to the present invention comprises an optically active isomeric class of compound according to Formula I, wherein the tetrahedral carbon atom in the 1-position is in the S configuration.

It has been found that the S(+) enantiomer of a compound of Formula I possesses greater histamine H₂-receptor antagonist activity than its R(-) isomer. This increased activity is exemplified by S(+)-3-amino-5-[3-[5-(1-piperidinyl-1,2,3,4-tetrahydronaphthyloxy)]propylamino]-1-methyl-1H-1,2,4-triazole, the H₂-antagonist activity of which is about ten times that of its R(-) isomer. The separation of activity may be measured in the pharmacological tests described herein above including: the guinea pig atria test; the lumen perfused stomach test; the aspirin induced ulcer test; and the pylorus-ligated rat test.

In particular, the compounds according to Formulae I to VI are useful: in the treatment and prevention of hyperacidity and gastrointestinal ulceration; for decreasing gastrointestinal acid secretion in mammals; and for enhancing the gastrointestinal resistance to gastrointestinal irritants in humans and other mammals.

For all these purposes, the compounds of this invention can be normally administered orally or parenterally. Oral administration is preferred.

The compounds according to the invention, preferably in the form of a salt, may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Such compositions may also contain if required other active ingredients, for example, H₁-antagonists, or known antacids such as aluminum hydroxide, magnesium hydroxide, magnesium trisilicate, aluminum glycinate, or calcium carbonate. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for intramuscular and subcutaneous injection purposes. The aqueous solutions, including those of the salts dissolved in pure distilled water, are also useful for intravenous injection purposes, provided that their pH is properly adjusted, suitably buffered, and made isotonic with sufficient saline or glucose.

The dosage regimen in carrying out the methods of this invention is that which insures maximum therapeutic response until improvement is obtained and thereafter the minimum effective level which gives relief. Thus, in general, the dosages are those that are therapeutically effective in the treatment of gastrointestinal disease conditions or symptoms, such as duodenal and peptic ulcer. In general, the dose can be between about 0.1 mg/kg and 100 mg/kg (preferably in the range of 1 to 20 mg/kg), bearing in mind, of course, that in selecting the appropriate dosage in any specific case, consideration must be given to the patient's weight, general health, age, and other factors which may influence response to the drug. The daily dose can range from 1 to 4 times a day.

We claim:

1. A compound of the formula:

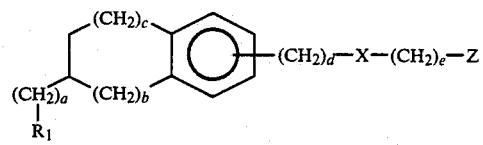

wherein:
a is 0, 1 or 2;
b is 0 or 1;
c is 1-b, 2-b or 3-b
d is 0 or 1;
e is 2, 3 or 4;
X is oxygen, sulfur,

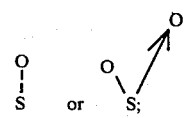

Z is —NHR₄;

$R_1$ is —$NR_2R_3$;

$R_2$ and $R_3$ are each independently H or alkyl, or both together with the nitrogen to which they are attached form a 5, 6 or 7-membered ring which may include one to three additional hetero atoms of N, O or S;

$R_4$ is

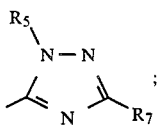

$R_5$ is H or lower alkyl;

$R_7$ is hydrogen, lower alkyl, lower alkenyl, aryl, arloweralkyl, hydroxyloweralkyl, acyloxyloweralkyl, loweralkoxyloweralkyl, aryloxyalkyl, aroyloxyalkyl, aralkyloxyalkyl, aminoalky, alkylaminoalkyl, dialkylaminoalkyl, hydroxy, alkoxy, alkylthio or halogen or $NR_8R_9$;

$R_8$ is hydrogen, loweralkyl,, lower alkenyl or arloweralkyl;

$R_9$ is hydrogen, $COR_{10}$, $SO_2R_{11}$ or

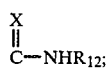

$R_{10}$ is hydrogen, loweralkyl, aryl, arloweralkyl, loweralkoxy, heteroaryl, or monocyclic heteroarylalkyl;

$R_{11}$ is lower alkyl or aryl;

$R_{12}$ is hydrogen, lower alkyl, cycloloweralkyl, aryl or arloweralkyl; wherein any aryl is phenyl or substituted phenyl and any aroyl is benzoyl;

or a pharmaceutically acceptable salt thereof.

2. A compound according to claim 1 wherein:
a is 0;
b is 0;
d is 0;
e is 3; and
X is oxygen.

3. A compound of the formula

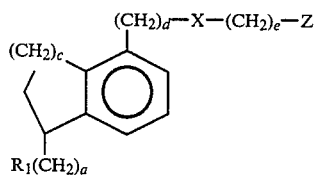

wherein:
a is 0, 1 or 2;
c is 1, 2 or 3;
d is 0 or 1;
e is 2, 3 or 4;
X is oxygen or sulfur;
Z is —$NHR_4$;
$R_1$ is —$NR_2R_3$;

$R_2$ and $R_3$ are each independently H or alkyl, or both together with the nitrogen to which they are attached form a 5, 6 or 7-membered ring which may include one to three additional hetero atoms of N, O or S;

$R_4$ is

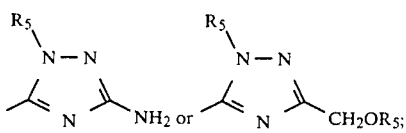

$R_5$ is H or lower alkyl;

or a pharmaceutically acceptable salt thereof.

4. A compound of the formula

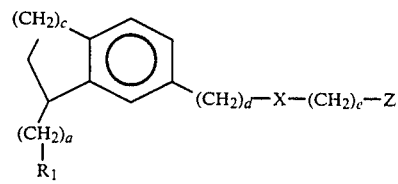

wherein:
a is 0, 1 or 2;
c is 1, 2 or 3;
d is 0 or 1;
e is 2, 3 or 4;
X is oxygen or sulfur;
Z is —$NHR_4$;
$R_1$ is —$NR_2R_3$;

$R_2$ and $R_3$ are each independently H or alkyl, or both together with the nitrogen to which they are attached form a 5, 6 or 7-membered ring which may include one to three additional hetero atoms of N, O or S;

$R_4$ is

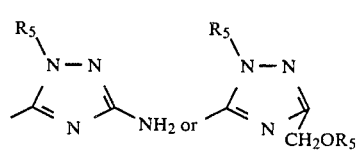

$R_5$ is H or lower alkyl;

or a pharmaceutically acceptable salt thereof.

5. A compound of the formula

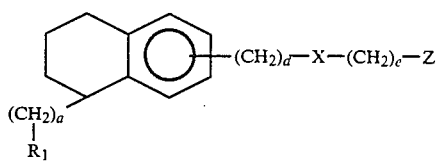

wherein:
a is 0, 1 or 2;
d is 0 or 1;
e is 2, 3 or 4;
X is oxygen or sulfur;
Z is —$NHR_4$;
$R_1$ is —$NR_2R_3$;

$R_2$ and $R_3$ are each independently H or alkyl, or both together with the nitrogen to which they are attached form a 5, 6 or 7-membered ring which may include one to three additional hetero atoms of N, O or S; $R_4$ is

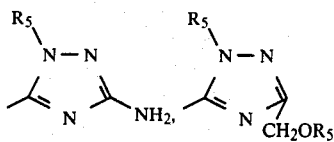

$R_5$ is H or lower alkyl;
or a pharmaceutically acceptable salt thereof.

6. A compound of the formula

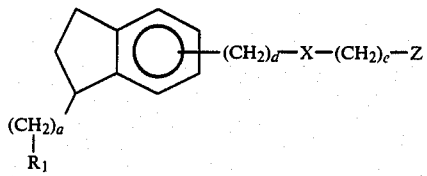

wherein:
a is 0, 1 or 2;
d is 0 or 1;
e is 2, 3 or 4;
X is oxygen or sulfur;
Z is —$NHR_4$;
$R_1$ is —$NR_2R_3$;
$R_2$ and $R_3$ are each independently H or alkyl, or both together with the nitrogen to which they are attached form a 5, 6 or 7-membered ring which may include one to three additional hetero atoms of N, O or S;
$R_4$ is

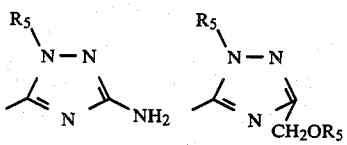

$R_5$ is H or lower alkyl;
or a pharmaceutically acceptable salt thereof.

7. A compound according to claim 5 wherein:
a and d are 0;
e is 3; and
X is oxygen.

8. A compound according to claim 5 wherein:
a is 0;
d is 1;
e is 2; and
X is sulfur.

9. A compound according to claim 5, which is 3-Amino-5-[4-[5-[1-(1-piperidinyl)-1,2,3,4-tetrahydronaphthyloxy]] butylamino]-1-methyl-1H-1,2,4-triazole or a pharmaceutically acceptable salt thereof.

10. A compound according to claim 5, which is 3-Amino-5-[3-[5-[1-(1-piperidinylmethyl)-1,2,3,4-tetrahydronaphthyloxy)]] propylamino]-1-methyl-1H-1,2,4-triazole or a pharmaceutically acceptable salt thereof.

11. A compound according to claim 6, which is 3-hydroxymethyl-5-[3-[4-[1-(1-piperidinyl)indanyloxy]]-propylamino]-1-methyl-1H-1,2,4-triazole or a pharmaceutically acceptable salt thereof.

12. A compound according to claim 6, which is 3-hydroxymethyl-5-[3-[5-[1-(1-piperidinyl)-1,2,3,4-tetrahydronaphthyloxy]]propylamino]-1,2,4-triazole or a pharmaceutically acceptable salt thereof.

13. A compound according to claim 1, wherein the carbon atom to which the $R_1$—$(CH_2)_a$-group is attached is in the S configuration.

14. A compound according to claim 5, which is the S(+) enantiomeric base or a pharmaceutically acceptable salt thereof.

15. A compound according to claim 6, which is the S(+) enantiomeric base or a pharmaceutically acceptable salt thereof.

16. A compound according to claim 1, wherein the carbon atom to which the $R_1$—$(CH_2)_a$- group is attached is in the R— configuration.

17. A compound according to claim 1, which is the racemic mixture of the base or a pharmaceutically acceptable salt thereof.

18. A method for decreasing acid secretion in the gastrointestinal tract of mammals by administering thereto an anti-secretory effective amount of a compound according to claim 1.

19. A method for the treatment of gastrointestinal hyperacidity and ulceration in a mammal comprising administering thereto an effective amount of a compound according to claim 1.

20. A method for enhancing the gastrointestinal resistance to gastrointestinal irritants in humans and mammals comprising administering thereto an effective cytoprotective amount of a compound of the formula according to claim 1.

21. A pharmaceutical composition wherein the active ingredient is a compound according to claim 1 in admixture with a pharmaceutical carrier.

* * * * *